United States Patent
Taniguchi et al.

(10) Patent No.: US 7,297,698 B2
(45) Date of Patent: Nov. 20, 2007

(54) N-PHENYL-(2R,5S) DIMETHYLPIPERAZINE DERIVATIVE

(75) Inventors: Nobuaki Taniguchi, Tsukuba (JP);
Masakazu Imamura, Tsukuba (JP);
Masahiko Hayakawa, Tsukuba (JP);
Kenichi Kawaguchi, Tsukuba (JP);
Takenori Kimura, Takahagi (JP); Isao Kinoyama, Tsukuba (JP); Hiroyuki Kaizawa, Tsukuba (JP); Minoru Okada, Tsukuba (JP); Takashi Furutani, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 428 days.

(21) Appl. No.: 10/521,119

(22) PCT Filed: Jul. 11, 2003

(86) PCT No.: PCT/JP03/08860

§ 371 (c)(1),
(2), (4) Date: Jan. 12, 2005

(87) PCT Pub. No.: WO2004/007471

PCT Pub. Date: Jan. 22, 2004

(65) Prior Publication Data

US 2005/0261303 A1 Nov. 24, 2005

(30) Foreign Application Priority Data

Jul. 12, 2002 (JP) .............................. 2002-203690

(51) Int. Cl.
*A61K 31/4965* (2006.01)
*C07D 403/00* (2006.01)

(52) U.S. Cl. .................................. 514/252.14; 544/295

(58) Field of Classification Search ..................... None
See application file for complete search history.

(56) References Cited

U.S. PATENT DOCUMENTS 3,875,229 A  4/1975  Gold
6,673,799 B1  1/2004  Taniguchi et al.

FOREIGN PATENT DOCUMENTS

| EP | 0 100 172 A1 | | 2/1984 |
| JP | 49-81332 A | | 8/1974 |
| JP | 2001-328938 | * | 11/2001 |
| JP | 2001-328938 A | | 11/2001 |
| WO | WO 95/19770 A1 | | 7/1995 |
| WO | WO 00/17163 A1 | | 3/2000 |

OTHER PUBLICATIONS

Koichiro Akakura et al., "Steroidal and Nonsteroidal Antiandrogens: Chemical Structures, Mechanism of Action and Clinical Applications" Nihon Rinsyo (1998), vol. 56, No. 8, pp. 2124-2128.
International Search Report dated Aug. 8, 2003.

* cited by examiner

*Primary Examiner*—Zachary C. Tucker
*Assistant Examiner*—Erich A. Leeser
(74) *Attorney, Agent, or Firm*—Sughrue Mion Pllc.

(57) ABSTRACT

The present invention relates to a novel N-phenyl-(2R,5S) dimethylpiperazine derivatives useful as antiandrogenic agent which exhibits a sufficient prostate gland reducing effect as compared with conventional compounds and are excellent in oral activity. The compound of the present application is useful in preventing or treating prostate cancer, benign prostatic hyperplasia, and the like. The present invention also provides a novel intermediate useful in producing the compound of the present invention.

7 Claims, No Drawings

N-PHENYL-(2R,5S) DIMETHYLPIPERAZINE DERIVATIVE

TECHNICAL FIELD

The present invention relates to a novel N-phenyl-(2R,5S)dimethylpiperazine derivative and a salt thereof useful as a medicament, particularly an antiandrogenic agent, a medicament thereof, and an intermediate thereof.

BACKGROUND ART

Androgen which is one kind of steroid hormones is secreted from the testis and adrenal cortex and causes an androgenic hormone action. Androgen is taken in a target cell to act on an androgen receptor and the receptor combined with androgen forms a dimer. Then, the dimer binds to an androgen-response-element on a DNA to accelerate synthesis of an m-RNA and to induce proteins which direct androgenic actions, whereby various actions are expressed in vivo (Prostate Suppl., 6, 1996, 45-51, Trends in Endocrinology and Metabolism, 1998 9(8), 317-324).

Diseases in which androgen acts as an aggravating factor include prostate cancer, benign prostatic hyperplasia, virilism, hirsutism, baldness, acne, seborrhea, and the like. Therefore, antiandrogenic agents have been employed for treating these diseases which may be attributed to androgen.

Antiandrogenic agents, which have substrate resembling steroidal structure or non-steroidal structure are currently used in the clinical field. Though chlormadinone acetate and the like are known as the steroidal antiandrogen, it is known that, since separation of actions of these compounds from other steroids having similar structures is not sufficient, they cause changes in the blood hormone level and induces serious side effects such as reduction of libido and the like (Jpn. J. Clin. Oncol., 1993, 23(3), 178-185).

On the other hand, as the compounds each having a non-steroidal structure, acylanilide derivatives such as flutamide (Patent Document 1) and bicalutamide (Patent Literarues 2 and 3) are known but these compounds are not sufficient in antiandrogenic action. Therefore, in the treatment of prostate cancer, combination therapy with an LH-RH agonist is generally adopted (Non-Patent Document 1).

The compounds of the present invention are compounds which fall within the range of the following general formula defined in claims of Patent Document 4:

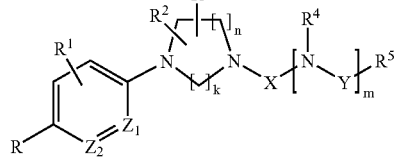

for the symbols in the formula, refer to Patent Document 4, and have the same pharmacological action but the compounds in present invention are not disclosed or suggested as specific examples in the above Document. The compounds having the most strong activity described in the above Document have problems of agonistic action, body weight loss, and the like other than the main effect. Also, the compound in the above Document having no these side effects and having a strong activity exhibits a low oral activity. Thus, it has been desired to develop a pharmaceutical agent which further improves these points.

[Patent Document 1]
  JP-A-49-81332
[Patent Document 2]
  GB 8221421
[Patent Document 3]
  International Publication WO 95/19770 Pamphlet
[Patent Document 4]
  International Publication WO 00/17163 Pamphlet
[Non-Patent Document 1]
  Nihon Rinsho 1998, 56(8), 2124-2128

DISCLOSURE OF THE INVENTION

As a result of the extensive studies for solving the problems of the compounds disclosed in Patent Document 4, the present inventors have found that N-phenyl-(2R,5S) dimethylpiperazine derivatives represented by the general formula (I) to be mentioned below, i.e., compounds not specifically disclosed in Patent Document 4 and novel N-phenyl-(2R,5S)dimethylpiperazine derivatives whose phenyl group is trisubstituted have an excellent prostate gland reducing effect by oral administration without body weight loss. Thus, they have accomplished the present invention.

Since the compounds of the present invention are not specifically disclosed by examples and the like in the above document and the compounds of the present invention show a good pharmacokinetics in the body, it is unexpected that the compounds exhibit an excellent prostate gland reducing effect which is not expectable based on the in vitro activities.

An object of the present invention is to provide a novel N-phenyl-(2R,5S)dimethylpiperazine derivative and a salt thereof useful as a medicament, particularly an antiandrogenic agent.

Specifically, it relates to the N-phenyl-(2R,5S)dimethylpiperazine derivatives or salts thereof shown in the following (1) to (4).

(1) An N-phenyl-(2R,5S)dimethylpiperazine derivative represented by the following general formula (I) or a salt thereof:

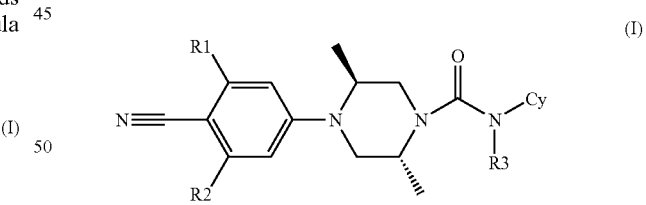

wherein the symbols in the formula have the following meanings:
$R^1$: Cl, F, Br, —CN, —CH$_3$, —CF$_3$, or —O-lower alkyl
$R^2$: H, F, or —OCH$_3$
$R^3$: H or lower alkyl
Cy: a group represented by the following a) to e) groups,
a) -benzene (monosubstituted by —CN, —COCH$_3$, or —OCF$_3$)
b) -benzene (phenyl monosubstituted by a group selected from —SCF$_3$, —OCH$_3$, —NO$_2$, and 1-CN-cyclopropyl-1-yl, or disubstituted by groups one of which is —CN and another one of which is selected from —OCF$_3$, —OCH$_3$, —CH$_3$, —CF$_3$, and —Cl)

c) -pyridine (substituted by —CN, —CF₃, halogen, —OCH₂CF₃, or cyclopropyl)
d) -pyrimidine (monosubstituted by lower alkyl or cyclopropyl)
e) -imidazopyridine (optionally substituted by lower alkyl)
  -benzopyrazine (optionally substituted by lower alkyl or cycloalkyl)
  -quinoxaline (optionally substituted by —O-lower alkyl or morpholinyl)
  -quinoline (optionally substituted by lower alkyl or morpholinyl)
  -benzothiazole (optionally substituted by lower alkyl)
  -isoquinoline
  -benzothiadiazole (optionally substituted by lower alkyl)
  -indolidine or tetrahydrobenzofuran (optionally substituted by oxo)

provided that Cy represents a group other than the c) group when $R^1$ is —CF₃ and $R^2$ is H.

(2) The N-phenyl-(2R,5S)dimethylpiperazine derivative or salt thereof according to the (1) above, wherein $R^1$ is Cl, F, Br, —CN, —CH₃, or —O-lower alkyl and $R^3$ is H.

(3) The N-phenyl-(2R,5S)dimethylpiperazine derivative or salt thereof according to the (2) above, wherein Cy is a group selected from the c) group.

(4) A compound selected from (2R,5S)-4-(3-chloro-4-cyanophenyl)-N-(2-cyclopropylpyrimidin-5-yl)-2,5-dimethylpiperazine-1-carboxamide; (2R,5S)-4-(3-chloro-4-cyanophenyl)-N-(6-cyano-3-pyridyl)-2,5-dimethylpiperazine-1-carboxamide; (2R,5S)-4-(4-cyano-3-methoxyphenyl)-2,5-dimethyl-N-(6-trifluoromethyl-3-pyridyl)piperazine-1-carboxamide; (2R,5S)-4-(3-bromo-4-cyanophenyl)-2,5-dimethyl-N-(6-trifluoromethyl-3-pyridyl)piperazine-1-carboxamide; and (2R,5S)-4-(4-cyano-3-trifluoromethylphenyl)-N-(2-cyclopropylpyrimidin-5-yl)-2,5-dimethylpiperazine-1-carboxamide, or a salt thereof.

Moreover, (5) to (8) relate to pharmaceutical uses of the N-phenyl-(2R,5S)dimethylpiperazine derivative and therapeutic methods.

(5) A pharmaceutical composition comprising the N-phenyl-(2R,5S)dimethylpiperazine derivative according to the above (1) or a pharmaceutically acceptable salt thereof as an active ingredient.

(6) A prostate cancer-treating agent comprising a therapeutically effective amount of the N-phenyl-(2R,5S)dimethylpiperazine derivative according to the above (1) or a pharmaceutically acceptable salt thereof as an active ingredient.

(7) Use of N-phenyl-(2R, 5S) dimethylpiperazine derivative according to the above (1) or a pharmaceutically acceptable salt thereof for manufacturing a medicament for treating prostate cancer which comprises a therapeutically effective amount of the same as an active ingredient.

(8) A method for treating prostate cancer which comprises administering a therapeutically effective amount of the N-phenyl-(2R,5S)dimethylpiperazine derivative according to the above (1) or a pharmaceutically acceptable salt thereof.

Furthermore, the following relates to an intermediate useful in producing the N-phenyl-(2R,5S)dimethylpiperazine derivatives of the present invention.

(9) A compound represented by the following general formula (IIIa) or a salt thereof:

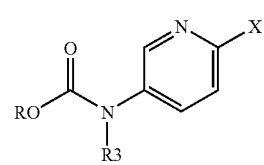

(IIIa)

wherein the symbols in the formula have the following meanings:
$R^3$: H or lower alkyl, and
1) when X is F, Br, —CN, or —CF₃,
  R: lower alkyl, halogeno-lower alkyl, phenyl optionally substituted by nitro, or succinimide optionally substituted by OH,
  provided that, when R is tert-butyl, X represents —CN, or
2) when X is Cl,
  R: halogeno-lower alkyl, phenyl optionally substituted by nitro, or succinimide optionally substituted by OH.

BEST MODE FOR CARRYING OUT THE INVENTION

The following will further describe the present invention.
The compounds represented by the general formula (I) will be further described in the following.
In the definition of the general formulae herein, the term "lower" means a linear or branched carbon chain having from 1 to 6 carbon atoms, unless otherwise specifically indicated.

"Lower alkyl" is $C_{1-6}$ alkyl, preferably $C_{1-4}$ alkyl such as methyl, ethyl, propyl, isopropyl or tert-butyl, more preferably $C_{1-3}$ alkyl.

"Halogen" includes, for example, fluorine, chlorine, bromine, and iodine atoms.

"Halogeno-lower alkyl" is a group wherein any hydrogen atom of the above lower alkyl is substituted with the above halogen(s), and includes preferably trifluoromethyl, 2,2,2-trifluoroethyl, and the like.

"Cycloalkyl" means cycloalkyl having 3 to 8 carbon atoms and specifically includes cyclopropyl, cyclobutyl, cyclopentyl, cyclohexyl, and the like. Preferred is cycloalkyl having 3 to 6 carbon atoms.

"Aryl" is an aromatic hydrocarbon ring having 6 to 10 carbon atoms, and is specifically benzene or naphthalene.

As the Cy, preferred is a pyridin-3-yl group where the 6-position of the pyridine ring is substituted with —CN, —CF₃, or halogen.

The following production method is preferred as a process for producing the compounds of the present invention:

Namely, a process for producing the N-phenyl-(2R,5S) dimethylpiperazine derivative represented by the general formula (I) or salt thereof:

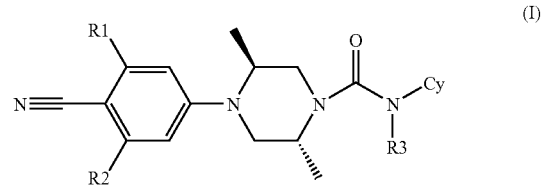

(I)

wherein the symbols in the formula are as mentioned below, which comprises reacting a compound represented by the following general formula (II):

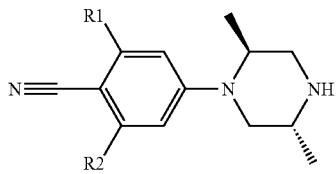
(II)

wherein the symbols in the formula have the following meanings:
R¹: Cl, F, Br, —CN, —CH₃, —CF₃, or —O-lower alkyl
R²: H, F, or —OCH₃, with a compound represented by the following general formula (III) or a reactive derivative thereof:

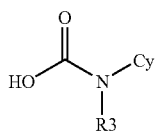
(III)

wherein the symbols in the formula have the following meanings:
R³: H, or lower alkyl
Cy: a group represented in the following a) to e) groups,
a) -benzene (monosubstituted by —CN, —COCH₃, or —OCF₃)
b) -benzene (phenyl monosubstituted by a group selected from —SCF₃, —OCH₃, —NO₂, and 1-CN-cyclopropyl-1-yl, or disubstituted by groups one of which is —CN and another one of which is selected from —OCF₃, —OCH₃, —CH₃, —CF₃, and —Cl)
c) -pyridine (substituted by —CN, —CF₃, halogen, —OCH₂CF₃, or cyclopropyl)
d) -pyrimidine (monosubstituted by lower alkyl or cyclopropyl)
e) -imidazopyridine (optionally monosubstituted by lower alkyl)
-benzopyrazine (optionally substituted by lower alkyl or cycloalkyl)
-quinoxaline (optionally substituted by —O-lower alkyl or morpholinyl)
-quinoline (optionally substituted by lower alkyl or morpholinyl)
-benzothiazole (optionally substituted by lower alkyl)
-isoquinoline
-benzothiadiazole (optionally substituted by lower alkyl).
-indolidine or tetrahydrobenzofuran (optionally substituted by oxo).

The above production method is a process for obtaining an optically active compound (I)

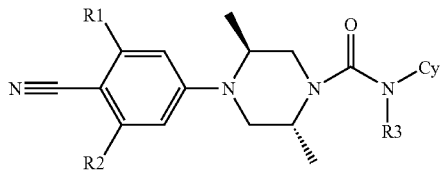
(I)

of the present invention efficiently by reacting the compound represented by the general formula (II) which is an optically active starting material with the compound represented by the general formula (III).

According to the present production method, the compound (I) of the present invention excellent in oral activity having less side effects and having an excellent prostate gland reducing effect can be obtained.

The reactive derivative of the compound (III) includes alkyl esters of carbamic acid, such as methyl ester, ethyl ester, isobutyl ester, and tert-butyl ester, halogeno-lower alkyl esters of carbamic acid, such as trifluoromethyl ester and 2,2,2-trifluoroethyl ester, phenyl esters such as phenyl ester, p-nitrophenyl ester, and 2,4-dinitrophenyl ester, active esters of carbamic acid derived from alcohols having good leaving ability, e.g., N-hydroxyamine-based compounds such as 1-hydroxysuccinimide and 1-hydroxybenzotriazole, carbamoyl halides such as carbamoyl chloride and carbamoyl bromide, carbamoyl azide, symmetrical acid anhydrides, mixed acid anhydrides, e.g., organic acid-based mixed acid anhydrides obtainable by the reaction with alkyl halocarboxylates such as alkyl carbonyl halides or pivaloyl halides, phosphate-based mixed acid anhydride obtainable by the combination of an organophosphorus compound such as triphenylphosphine with an activating agent such as N-bromosuccinimide, and isocyanates.

Among the compounds (I) of the present invention, there exist geometrical isomers based on an amide bond. Depending on the kind of substituents, there are cases that the compounds have one or more asymmetric centers of carbon, nitrogen, and sulfur, or axial asymmetries and there exist optical isomers such as (R)- and (S)-isomers, racemates, diastereomers, and the like based on them. Moreover, there may exist geometrical isomers, e.g., (Z)-isomers, (E)-isomers, and the like since the compounds have a double bond depending on the type of the substituents, and further cis-isomers, trans-isomers, and the like based on a ring such as cyclohexane. The present invention encompasses all such isomers isolated and their mixtures.

The compounds of the present invention form salts. Specifically, the salts are acid addition salts with inorganic acids or organic acids or salts with inorganic or organic bases and preferred are pharmaceutically acceptable salts. Specifically, such salts include addition salts with mineral acids such as hydrochloric acid, hydrobromic acid, hydroiodic acid, sulfuric acid, nitric acid, and phosphoric acid; or with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, and benzenesulfonic acid; or acidic amino acids such as aspartic acid and glutamic acid; the salts with inorganic bases such as sodium, potassium, magnesium, calcium, aluminum, and lithium; with organic bases such as methylamine, ethylamine, and ethanolamine; with basic amino acids such as lysine and ornithine; and the like. Furthermore, the salts may be ammonium salts. The ammonium salts may be prepared from specifically lower alkyl halides, lower alkyl triflates, lower alkyl tosylates, benzyl halides, or the like, preferably methyl iodide or benzyl chloride.

Furthermore, the compounds of the present invention may sometimes form hydrates and solvates with ethanol or the like, and the compounds may have crystalline polymorphism in some cases of the compounds, all of them being encompassed.

The compounds of the present invention further include pharmaceutically acceptable prodrugs. The groups that form the pharmaceutically acceptable prodrugs of the compounds of the present invention are groups described in Prog. Med. 5:2157-2161 (1985) and groups described in "Iyakuhinn no Kaihatsu (Development of Medicines) published by Hirokawa Shoten, 1990, Vol. 7, Bunshi Sekkei (Molecular Design), pp. 163-198. Specifically, they are groups capable of being converted into primary amines, secondary amines, OH, COOH and others of the present invention through hydrolysis or solvolysis or under physiological conditions. Examples of prodrugs for an OH group include —OC(O)-optionally substituted lower alkyl-C(O)OR(R represents H or lower alkyl, the same shall apply hereunder), —OC(O)-optionally substituted lower alkenylene-C(O)OR, —OC(O)-optionally substituted aryl, —OC(O)-lower alkyl-O-lower alkyl-C(O)OR, —OC(O)—C(O)R, —OC(O)-optionally substituted lower alkyl, —OSO$_2$-optionally substituted lower alkyl-C(O)OR, —O-phthalidyl, 5-methyl-1,3-dioxolen-2-on-4-yl-methyloxy, and the like.

The compounds (I) of the present invention and the pharmaceutically acceptable salts thereof are useful as treating agents for diseases in which androgen acts as a aggravating factor, such as prostate cancer, benign prostatic hyperplasia, virilism, hirsutism, baldness, acne, and seborrhea, based on their excellent antiandrogenic action and oral activities.

(Production Methods)

First Production Method

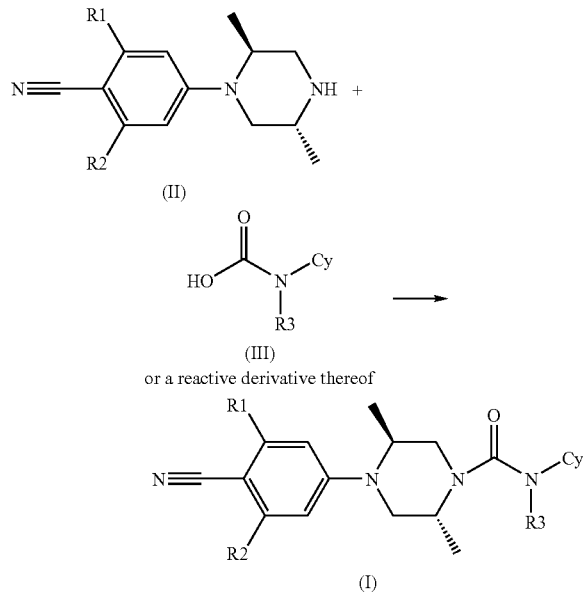

wherein the symbols in the formula are as mentioned above, the same shall apply hereunder.

The present production method is a process for producing the compound (I) of the present invention by reacting a substituted amine represented by the general formula (II) or a salt thereof with a compound represented by the general formula (III) or a reactive derivative thereof and, when there exists a protective group, removing the protective group.

Particularly, in the present invention, a condensation reaction with an isocyanate, an alkyl ester, halogeno-lower alkyl ester, a phenyl ester or an active ester of the carbamic acid, the active ester being obtainable from 1-hydroxysuccinimide is advantageous.

Moreover, it is possible to obtain (I) directly by treating a carboxylic acid convertible into (III) through a rearrangement reaction with DPPA in the presence of (II) to generate an isocyanate in situ. This method is advantageous in the case that the isocyanate derived from the corresponding carboxylic acid is unstable or in a similar case.

On the other hand, it is suitable to use a condensing agent such as dicyclohexylcarbodiimide, carbonyldiimidazole (CDI), diphenylphosphoryl azide (DPPA), diethylphosphoryl cyanide, or 1-ethyl-3-(3-dimethylaminopropyl)carbodiimide hydrochloride in the case that thea carboxylic acid is reacted as a free acid or the active ester is reacted without isolation.

The reaction is conducted usually in an organic solvent inert to the reaction, for example, a halogenated hydrocarbon such as dichloromethane, dichloroethane or chloroform; an aromatic hydrocarbon such as benzene, toluene or xylene; an ether such as ether or tetrahydrofuran (THF); an ester such as ethyl acetate; or acetonitrile, N,N-dimethylformamide (DMF), N,N-dimethylacetamide, N-methylpyrrolidone, or dimethylimidazolidinone (DMI), which may vary depending on the reactive derivative and the condensing agent to be used, under cooling, under from cooling to room temperature, or under from cooling to heating according to the reactive derivative.

At the reaction, it is sometimes advantageous for smooth progress of the reaction to use the substituted amine (II) excessively, or to conduct the reaction in the presence of a base such as N-methylmorpholine, trimethylamine, triethylamine, N,N-dimethylaniline, pyridine, DMAP, picoline, lutidine, colidine, 1,8-diazabicyclo[5.4.0]-7-undec-7-ene (DBU), 1,5-diazabicyclo[4.3.0]non-5-ene (DBN), 1,4-diazabicyclo[2.2.2]octane (DABCO), 1,4-dimethylpiperadine, sodium hydride (NaH), lithium diisopropylamide (LDA), potassium carbonate; cesium carbonate, sodium-carbonate, or sodium-hydrogen carbonate. Also, it is possible to accelerate the reaction by incorporating a phase transfer catalyst such as tetrabutylammonium bromide or a crown ether such as 18-crown-6 or 15-crown-5. Moreover, pyridine or the like can be used also as a solvent.

At this time, there are cases that an oxygen atom, a sulfur atom, a nitrogen atom, or the like present in the molecule is desirably combined with a protective group. As such protective groups, there can be mentioned protective groups described in "Protective Groups in Organic Synthesis (2nd edition)", written by Greene and Wuts, which may be optionally selected and used depending on the reaction conditions.

In this regard, in the process for obtaining (I) by converting one of various carboxylic acids into a corresponding isocyanate through a known rearrangement reaction and then treating the isocyanate with the amine derivative (II), there may be a case involving risk due to a rapid exothermic reaction at the above rearrangement reaction, for example, in mass production. Therefore, (I) can be obtained more safely and efficiently by using various carbamate esters (III) instead of the isocyanates.

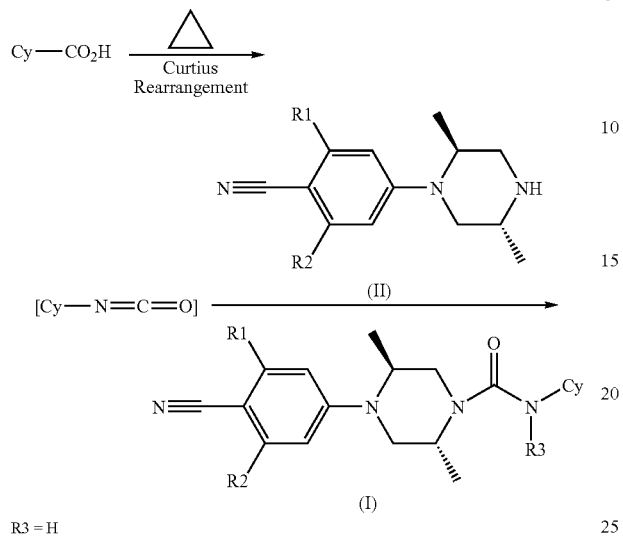

R3 = H

Second Production Method

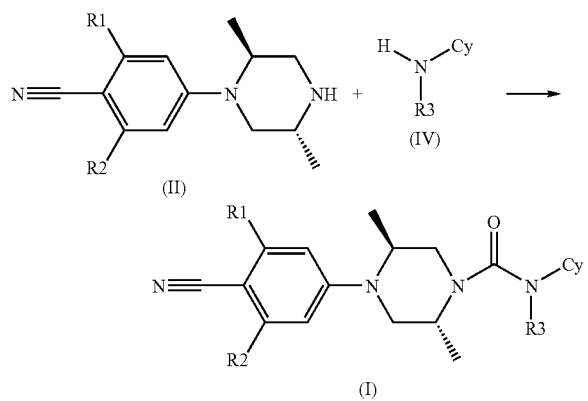

wherein the symbols in the formula are as mentioned above.

The present production method is a process for producing the compounds (I) of the present invention by reacting the substituted amine represented by the general formula (II) or salt thereof with carbonic acid or a reactive derivative equivalent to carbonic acid, then treating the resulting product with a compound represented by the general formula (IV) and, when there exists a protective group, removing the protective group.

As the reactive derivative equivalent to carbonic acid, use can be made of phosgene, phosgene dimer, triphosgene, CDI, N,N-succinimidyl carbonate (DSC), phenyl chlorocarbonate, or a known equivalent.

In this connection, at the reaction, it is possible to employ the conditions shown in the first production method.

The compounds of the present invention synthesized in accordance with the above production method can be converted into the other compounds of the present invention by converting functional groups or the like using known reactions.

Production Method 1 of Starting Material

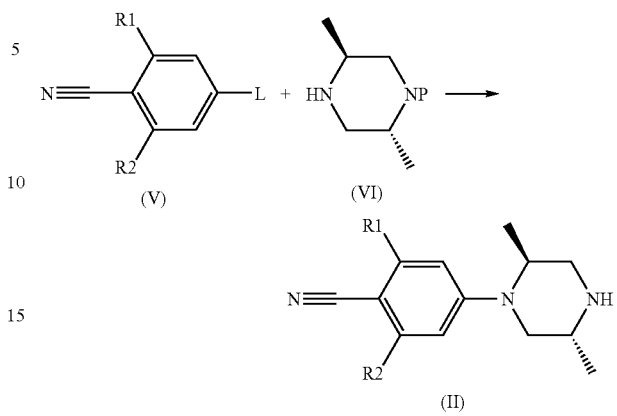

in the formula, L represents a functional group which can be replaced by the reaction with an amine, e.g., halogen such as fluorine, chlorine, bromine, or iodine, or trifluoromethanesulfonyloxy or benzenesulfonyloxy. Moreover, P represents a protective group of a nitrogen atom, such as benzyl, allyl, benzyloxycarbonyl, or tert-buthoxycarbonyl or a hydrogen atom.

The compound (II) for use in the present production method can be obtained by reacting a compound (V) with 2,5-trans-dimethylpiperadine or its N-substituted derivative (VI) and removing the protective group (P) by a suitable reaction. At this time, it is possible to synthesize an optically active (II) by using an optically active (VI). As the optically active (VI), the derivative where P is allyl, benzyl, or tert-butoxycarbonyl is known. Moreover, when (VI) is a racemic one or 2,5-trans-dimethylpiperazine, it is possible to obtain an optically active (II) by conducting the condensation reaction under an optically active environment. Alternatively, an optically active (II) can be obtained by optical resolution of the resulting racemic one. As a method for such optical resolution, it is possible to employ known optically active columns such as optical resolution columns CHIRAL-CEL OH-H and CHIIRALPAK AD-H manufactured by Daicel Chemical Industries, Ltd. Moreover, optical resolution using an optically active acid is also possible and, as optically active carboxylic acids to be used at this time, use can be made of organic acids such as tartaric acid, di-p-toluoyltartaric acid, dibenzoyltartaric acid, camphorsulfonic acid, and mandelic acid. Methods for such optical resolution are described in "Yuki Gosei Handbook (Handbook for Organic Synthesis)" edited by Society of Synthetic Organic Chemistry, Japan, Maruzen, Tokyo, 1990, P760 and the like. At the reaction, it is sometimes advantageous for smooth progress of the reaction to use (VI) excessively, or to conduct the reaction in the presence of an organic base such as N-methylmorpholine, trimethylamine, triethylamine, diisopropylethylamine, N,N-dimethylaniline, pyridine, DMAP, picoline, lutidine, 1,8-bistrimethylaminonaphthalene, DBU, DBN, DABCO, or LDA, or an inorganic base such as NaH, potassium carbonate, sodium carbonate, calcium carbonate, cesium carbonate, sodium hydrogen carbonate, or sodium hydroxide. Also, it is possible to accelerate the reaction by incorporating a phase transfer catalyst such as tetrabutylammonium bromide or a crown ether such as 18-crown-6 or 15-crown-5. Moreover, pyridine or the like can be used also as a solvent. Furthermore, it is also suitable to use an organometallic catalyst as a catalyst and, as such an example, use can be made of conditions described in Yang, Bryant H.; Buchwald, Stephen L., Journal of Organometallic Chemistry (1999), 576(1-2), 125-146, and the like conditions.

The reaction is conducted usually in an organic solvent inert to the reaction, such as a halogenated hydrocarbon such as dichloromethane, dichloroethane or chloroform; an aromatic hydrocarbon such as benzene, toluene, or xylene; an ether such as ether or tetrahydrofuran; an ester such as ethyl acetate; an alcoholic solvent such as ethanol or methanol; or acetonitrile, DMF, N,N-dimethylacetamide, N-methylpyrrolidone, DMI, or dimethyl sulfoxide, which may be varied depending on the substrate and conditions to be used, under cooling, under from cooling to room temperature, or under from cooling to heating according to the reactive derivative.

Production Method 2 of Starting Material

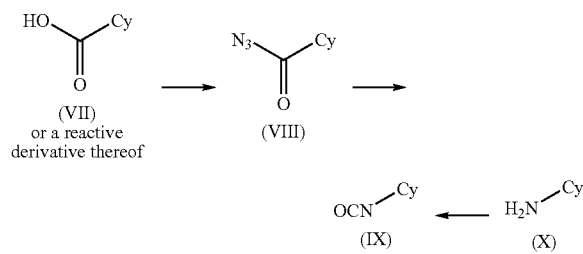

It is suitable to synthesize an isocyanate (IX), which is one of the reactive derivative (III) for use in the first production method, from a corresponding carboxylic acid or a carboxylic acid derivative such as amide or acid hydrazide by utilizing the known rearrangement reaction for example Curtius rearrangement. At the conversion of the carboxylic acid (VII) into the isocyanate (IX), it is advantageous to use a method of converting the carboxylic acid into a reactive derivative such as an acid chloride, a mixed acid anhydride, or an active-ester and then reacting it with sodium azide to obtain an acid azide (VIII), followed by heating or irradiation with a light, addition of an activating agent such as a Lewis acid, or the like. As conditions for activating such carboxylic acid, the method for activating the carbamic acid described in the first production method is applicable. Moreover, when DPPA or the like is used, it is easy to convert the carboxylic acid into the acid azide and, in some cases, it is possible to convert it into the isocyanate directly. On the other hand, it is possible to react a corresponding amine derivative (X) with phosgene or a phosgene equivalent to form the isocyanate. As such a phosgene equivalent, there may be mentioned phosgene dimer, triphosgene, CDI, chloro phenyl carbonate, DSC, a combination of di-tert-butyl dicarbonate and DMAP, or the like. Furthermore, it is possible to progress the reaction smoothly by adding a base or heating.

At these reactions, respective conditions shown in the first production method can be employed.

Production Method 3 of Starting Material

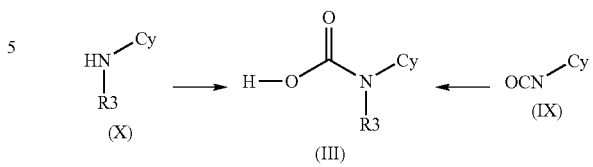

On the other hand, the compound (III) or its reactive derivative can be synthesized by reacting the corresponding amine derivative (X) with phosgene or a phosgene equivalent and then treating the resulting product with an alcohol, phenol derivative, or a nitrogen atom-protected N-hydroxyamine such as 1-hydroxysuccinimide. Also, it can be obtained by the reaction with one of various halocarbonates such as methyl chlorocarbonate and chloro phenyl carbonate or by a known reaction, e.g., treatment of the above isocyanate (IX) with an alcohol or phenol derivative. On the other hand, it is also suitable to synthesize it by reacting DSC with the amine derivative (X). At the present reaction, respective conditions shown in the first production method can be employed.

The compounds of the present invention thus produced may be isolated and purified as free base form, their salts, their hydrates, their solvates, or crystal polymorphic substances. Salts of the compounds (I) of the present invention can be also produced by subjecting the compound to an ordinary salt-forming reaction.

Isolation and purification may be effected by applying usual chemical operations such as extraction, concentration, removal by evaporation, crystallization, filtration, recrystallization, and various modes of chromatography.

Various isomers can be obtained by stereoselective synthesis using suitable starting compounds, reagents, or reaction conditions, or separated from each other by utilizing the difference in physical properties between the isomers. For example, optical isomers may be led to stereochemically pure isomers by selecting suitable starting materials or through optical resolution of racemic compounds (for example, a method of converting a racemic compound to a diastereomeric salt with an ordinary optically-active base, followed by optical resolution).

The pharmaceutical preparations that contain, as the active ingredient(s), one or more of the compounds of the present invention or their salts may be prepared by the use of a carrier, a vehicle, and other additives generally used in formulation.

The administration may be in any form of oral administration by means of tablets, pills, capsules, granules, powders or liquids, or parenteral administration by means of injections such as intravenous injections or intramuscular injections, or suppositories or subcutaneous preparation. Their dose may be suitably determined, depending on the symptom, the age and the sex of the patients to which they are administered, but is, in general, from about 0.01 to 50 mg/adult/day in the case of oral administration, and from about 0.001 to 5 mg/adult/day in the case of parenteral administration. This may be administered all at a time, or may be divided into a few portions for administration in 2 to 4 times.

As the solid composition for oral administration according to the present invention, employed are tablets, powders, granules, etc. In the solid composition of those types, one or more active substances are mixed with at least one inert diluent, such as lactose, mannitol, glucose, hydroxypropyl cellulose, microcrystalline cellulose, starch, polyvinylpyrrolidone, metasilicic acid, or magnesium aluminate. According to an ordinary manner, the composition may contain additives other than the inert diluents, for example, a lubricant such as magnesium stearate, a disintegrator such as calcium cellulose glycolate, a stabilizer such as lactose, and a dissolution promoter such as glutamic acid or aspartic acid. If necessary, the tablets or pills may be coated with a film of gastric or enteric substances such as sucrose, gelatin, hydroxypropyl cellulose, or hydroxypropylmethyl cellulose phthalate.

The liquid composition for oral administration includes pharmaceutically acceptable emulsions, solutions, suspensions, syrups, elixirs and the like, which contain conventional inert diluents such as pure water or ethanol. In addition to the inert diluents, the composition may further contain pharmaceutical aids such as wetting promoters and suspension promoters; and also sweeteners, flavorings, aromas and preservatives.

EXAMPLES

The following will describe the present invention in more detail with reference to Examples. The present invention is, by no means, not restricted to these Examples. In this connection, methods for producing the Starting compounds used in the Examples are illustrated as Reference Examples.

Reference Example 1-1

4-[(2S,5R)-4-Benzyl-2,5-dimethylpiperazin-1-yl]-2-fluorobenzonitrile

Into a solution of 25 ml of DMI and 25 ml of acetonitrile containing 10.0 g of (2R,5S)-1-benzyl-2,5-dimethylpiperazine obtained by the method of Reference Example 12-2 of Patent Document 4 were added 8.17 g of 2,4-difluorobenzonitrile and 31.9 g of cesium carbonate, followed by 2 days of stirring at 120° C. After the addition of ethyl acetate to the reaction solution, the mixture was washed with water and the organic layer was dried over anhydrous sodium sulfate. The solvent was removed by evaporation and the resulting residue was purified by silica gel column chromatography. An eluate eluted with hexane-ethyl acetate (85:15, v/v) was crystallized from chloroform to obtain 4.84 g of the title compound.

$^1$H-NMR (DMSO-$d_6$) δ: 0.98 (3H, d), 1.14 (3H, d), 2.25-2.36 (1H, m), 2.70-2.82 (1H, m), 2.98-3.12 (1H, m), 3.27-3.36 (1H, m), 3.50 (1H, d), 3.55-3.69 (2H, m) 4.00-4.18 (1H, m), 6.78 (1H, dd), 6.87 (1H, dd), 7.20-7.40 (5H, m), 7.55 (1H, t)

The following compounds were synthesized in the similar manner.

Reference Example 1-2

4-[(2S,5R)-4-Benzyl-2,5-dimethylpiperazin-1-yl]-2-chlorobenzonitrile $^1$H-NMR (DMSO-$d_6$) δ: 0.98 (3H, d), 1.14 (3H, d), 2.24-2.39 (1H, m), 2.76 (1H, dd), 3.27-3.36 (1H, m), 3.50 (1H, d), 3.55-3.69 (2H, m) 4.06-4.20 (1H, m), 6.91 (1H, dd), 7.06 (1H, d), 7.20-7.41 (5H, m), 7.61 (1H, d)

Reference Example 1-3

4-[(2S,5R)-4-Benzyl-2,5-dimethylpiperazin-1-yl]-2-methylbenzonitrile

To a solution of 3.81 g of (2R,5S)-1-benzyl-2,5-dimethylpiperazine in 20 ml of DMI were added 3.80 g of 4-fluoro-2-methylbenzonitrile and 7.27 g of diisopropylethylamine, followed by 2 days of stirring in a sealed tube at 210° C. After the addition of ethyl acetate to the reaction solution, the mixture was washed with water and the organic layer was dried over anhydrous sodium sulfate. The solvent was removed by evaporation and the resulting residue was purified by silica gel column chromatography to obtain 1.50 g of the title compound as a solid from an eluate eluted with hexane-ethyl acetate (85:15, v/v).

$^1$H-NMR (CDCl$_3$) δ: 1.07 (3H, d), 1.18 (3H, d), 2.29-2.36 (1H, m), 2.46 (3H, s), 2.87 (1H, dd), 3.03-3.14 (1H, m), 3.24-3.32 (1H, m), 3.36-3.45 (1H, m), 3.58 (1H, d), 3.64 (1H, d), 3.86-3.98 (1H, m), 6.61-6.68 (2H, m), 7.24-7.45 (6H, m)

Reference Example 2

4-[(2S,5R)-2,5-Dimethylpiperazin-1-yl]-2-methylbenzonitrile

Into 50 ml of dichloroethane was dissolved 1.81 g of 4-[(2S,5R)-4-benzyl-2,5-dimethylpiperazin-1-yl]-2-methylbenzonitrile, and then 1.62 g of 1-chloroethyl chlorocarbonate was added thereto, followed by heating under refluxing overnight. After the reaction solution was concentrated, 50 ml of methanol was added thereto, followed by heating under refluxing overnight. After the reaction solution was concentrated, water was added thereto, followed by washing with ether. The aqueous phase was made basic with a 1M sodium hydroxide aqueous solution, followed by extraction with ethyl acetate. The organic layer was dried over anhydrous sodium sulfate and then solvent was removed by evaporation to obtain 1.11 g of the title compound.

$^1$H-NMR (DMSO-$d_6$) δ: 1.03-1.09 (6H, m), 2.37 (3H, s), 2.45-2.53 (1H, m), 3.05-3.22 (4H, m), 3.70-3.82 (1H, m), 6.75-6.81 (1H, m), 6.83-6.88 (1H, m), 7.47 (1H, d)

Reference Example 3-1 tert-Butyl (2R,5S)-4-(4-cyano-3-fluorophenyl)-2,5-dimethylpiperazine-1-carboxylate Into a solution of 9.74 g of tert-butyl (2R,5S)-2,5-dimethylpiperazine-1-carboxylate in 25 ml of DMI and 25 ml of acetonitrile were added 5 g of 2,4-difluorobenzonitrile and 11.4 g of cesium carbonate, followed by 2 days of stirring at 120° C. The reaction solution was poured into water, followed by extraction with ethyl acetate. After the organic layer was washed with saturated saline, it was dried over anhydrous sodium sulfate. The solvent was removed by evaporation and the resulting residue was purified by silica gel column chromatography to obtain 4.66 g of the title compound from an eluate eluted with hexane-ethyl acetate (80:20, v/v).

$^1$H-NMR (CDCl$_3$) δ: 1.16 (3H, d), 1.23 (3H, d), 1.49 (9H, s) 3.23-3.48 (2H, m), 3.75-4.06 (2H, m), 4.17-4.30 (2H, m), 6.50 (1H, dd), 6.58 (1H, dd), 7.40 (1H, dd)

Reference Example 3-2 tert-Butyl (2R 5S)-4-(4-cyano-3-trifluoromethylphenyl)-2,5-dimethylpiperazine-1-carboxylate $^1$H-NMR (CDCl$_3$) δ: 1.17 (3H, d), 1.24 (3H, d), 1.49 (9H, s), 3.27-3.50 (2H, m), 3.70-4.06 (2H, m), 4.31 (1H, br s), 4.50 (1H, br s), 6.91 (1H, dd), 7.06 (1H, d), 7.62 (1H, d)

Reference Example 3-3 tert-Butyl (2R,5S)-4-(3-chloro-4-cyanophenyl)-2,5-dimethylpiperazine-1-carboxylate

FABMS 349 [M+H]$^+$

Reference Example 3-4 tert-Butyl (2R,5S)-4-(3-bromo-4-cyanophenyl)-2,5-dimethylpiperazine-1-carboxylate $^1$H-NMR (CDCl$_3$) δ: 1.15 (3H, d), 1.23 (3H, d), 1.49 (9H, s), 3.23-3.45 (2H, m), 3.70-4.10 (2H, m), 4.31 (1H, br s), 4.50 (1H, br s), 6.73 (1H, dd), 6.99 (1H, d), 7.44 (1H, d)

Reference Example 3-5 tert-Butyl (2R,5S)-4-(4-cyano-3,5-difluorophenyl)-2,5-dimethylpiperazine-1-carboxylate

FABMS 352 [M+H]$^+$

Reference Example 3-6 tert-Butyl (2R,5S)-4-(3,4-dicyanophenyl)-2,5-dimethylpiperazine-1-carboxylate $^1$H-NMR (CDCl$_3$) δ: 1.18 (3H, d), 1.23 (3H, d) 1.49 (9H, s), 2.73 (1H, dd), 3.11-3.19 (1H, m), 6.97 (1H, dd), 7.07 (1H, d), 7.57 (1H, d)

Reference Example 4-1

4-[(2S,5R)-4-Benzyl-2,5-dimethylpiperazin-1-yl]-2-methoxybenzonitrile

Into 20 ml of THF and 6 ml of methanol was dissolved 5.17 g of 4-[(2S,5R)-4-benzyl-2,5-dimethylpiperazin-1-yl]-2-fluorobenzonitrile, and then 9.83 g of potassium t-butoxide was added thereto, followed by stirring at room temperature overnight. A saturated ammonium chloride aqueous solution was added to the reaction solution, followed by extraction with chloroform. After the organic layer was dried over anhydrous sodium sulfate, the solvent was removed by evaporation and the resulting residue was purified by silica gel column chromatography to obtain 4.72 g of the title compound from an eluate eluted with hexane-ethyl acetate (80:20, v/v).

$^1$H-NMR (DMSO-d$_6$) δ: 1.01 (3H, d), 1.13 (3H, d), 2.24-2.34 (1H, m), 2.73-2.84 (1H, m), 3.00-3.12 (1H, m), 3.26-3.36 (1H, m), 3.46-3.58 (2H, m), 3.65 (1H, d), 3.86 (3H, s), 4.05-4.19 (1H, m), 6.46 (1H, d), 6.52 (1H, dd), 7.20-7.42 (6H, m)

The following Reference Examples were synthesized in the similar manner.

Reference Example 4-2 tert-Butyl (2R,5S)-4-(4-cyano-3-methoxyphenyl)-2,5-dimethylpiperazine-1-carboxylate

FABMS 346 [M+H]$^+$

Reference Example 4-3

4-[(2S,5R)-2,5-Dimethylpiperazin-1-yl]-2-fluoro-6-methoxybenzonitrile

The compound was synthesized in the similar manner as in Reference Example 4-1 using 4-[(2S,5R)-2,5-dimethylpiperazin-1-yl]-2,6-difluorobenzonitrile and 1 equivalent of potassium tert-butoxide.

FABMS 264 [M+H]$^+$

Reference Example 4-4

4-[(2S,5R)-2,5-Dimethylpiperazin-1-yl]-2,6-dimethoxybenzonitrile

The compound was synthesized in the similar manner as in Reference Example 4-1 using 4-[(2S,5R)-2,5-dimethylpiperazin-1-yl]-2,6-difluorobenzonitrile and 4.6 equivalents of potassium tert-butoxide.

FABMS 276 [M+H]$^+$

Reference Example 5 tert-Butyl (2R,5S)-4-(3-tert-butoxy-4-cyanophenyl)-2,5-dimethylpiperazine-1-carboxylate Into 20 ml of THF was dissolved 3.12 g of tert-butyl (2R,5S)-4-(3-fluoro-4-cyanophenyl)-2,5-dimethylpiperazine-1-carboxylate, and then 1.40 g of potassium tert-butoxide was added thereto, followed by heating under refluxing overnight. A saturated ammonium chloride aqueous solution was added to the reaction solution, followed by extraction with chloroform. After the organic layer was dried over anhydrous sodium sulfate, the solvent was removed by evaporation to obtain 1.11 g of the title compound.

$^1$H-NMR (CDCl$_3$) δ: 1.13 (3H, d), 1.24 (3H, d), 1.46 (9H, s) 1.49 (9H, s), 3.18-3.40 (2H, m), 3.70-4.05 (2H, m), 4.25-4.60 (2H, m), 6.46 (1H, d), 6.53 (1H, dd), 7.37 (1H, d)

Reference Example 6-1

4-[(2S,5R)-2,5-Dimethylpiperazin-1-yl]-2-fluorobenzonitrile

Into 150 ml of dichloromethane was dissolved 15.0 g of tert-butyl (2R,5S)-4-(4-cyano-3-fluorophenyl)-2,5-dimethylpiperazine-1-carboxylate, and then 30 ml of trifluoroacetic acid was added thereto, followed by stirring at room temperature overnight. After the reaction solution was removed by evaporation, 1M hydrochloric acid was added thereto, followed by washing with chloroform. The aqueous phase was made basic with a 5M sodium hydroxide aqueous solution, followed by extraction with chloroform. After the organic layer was dried over anhydrous magnesium sulfate, the solvent was removed by evaporation to obtain 12.0 g of the title compound.

$^1$H-NMR (CDCl$_3$) δ: 1.20 (3H, d), 1.21 (3H, d), 2.70 (1H, dd), 3.04-3.13 (1H, m), 3.22-3.37 (3H, m), 3.65-3.78 (2H, m), 6.59 (1H, dd), 6.62 (1H, dd), 7.40 (1H, dd)

Investigation of optical purity was conducted using a chiral column and the product was confirmed to be a pure optically active compound. HPLC retention time: 17.00 min. (column: CHIRALCEL OD-H manufactured by Daicel Chemical Industries, Ltd., size: 0.46 cm I.D.×25 cm L, mobile phase: hexane:isopropanol:diethylamine (600:400: 1). [vol. %], flow rate: 0.5 ml/min., temperature: 35° C., wavelength: 254 nm)

The following Reference Examples were synthesized in the similar manner.

In this connection, Reference Examples 6-1, 6-2, and 6-4 were also synthesized in a manner similar to Reference Example 2 and the values of their physical properties matched with the values of the physical properties described herein.

Reference Example 6-2

2-Chloro-4-[(2S,5R)-2,5-dimethylpiperazin-1-yl]benzonitrile $^1$H-NMR (CDCl$_3$) δ: 1.16-1.22 (6H, m), 2.69 (1H, dd), 3.00-3.36 (4H, m), 3.64-3.74 (1H, m), 6.75 (1H, dd), 6.87 (1H, d), 7.46 (1H, d).

HPLC retention time: 16.02 min. (the same analytical conditions as in Reference Example 6-1)

Reference Example 6-3

2-Bromo-4-[(2S,5R)-2,5-dimethylpiperazin-1-yl]benzonitrile $^1$H-NMR (CDCl$_3$) δ: 1.17 (3H, d), 1.20 (3H, d), 2.71 (1H, dd), 2.99-3.09 (1H, m), 3.22-3.35 (3H, m), 3.62-3.76 (2H, m), 6.79 (1H, dd), 7.05 (1H, d), 7.44 (1H, d)

HPLC retention time: 12.2 min. (column: CHIRALCEL OD-H manufactured by Daicel Chemical Industries, Ltd., size: 0.46 cm I.D.×25 cm L, mobile phase: hexane:isopropanol:diethylamine (700:300:5) [vol. %], flow rate: 0.5 ml/min., temperature: 40° C., wavelength: 230 nm)

Reference Example 6-4

4-[(2S,5R)-2,5-Dimethylpiperazin-1-yl]-2-methoxybenzonitrile $^1$H-NMR (CDCl$_3$) δ: 1.12 (3H, d), 1.17 (3H, d), 2.69 (1H, dd), 2.89 (1H, dd), 3.16-3.32 (4H, m), 3.48-3.59 (1H, m), 3.90 (3H, s), 6.41 (1H, d), 6.51 (1H, dd), 7.39 (1H, d)

HPLC retention time: 13.40 min. (the same analytical conditions as in Reference Example 6-1)

Reference Example 6-5

2-tert-Butoxy-4-[(2S,5R)-2,5-dimethylpiperazin-1-yl]benzonitrile $^1$H-NMR (CDCl$_3$) δ: 1.11 (3H, d), 1.17 (3H, d), 1.46 (9H, s), 2.60-2.76 (1H, m), 2.78-2.92 (1H, m), 3.13-3.35 (3H, m), 3.40-3.55 (1H, m), 6.60 (1H, d), 6.65 (1H, dd), 7.39 (1H, d)

Reference Example 6-6

4-[(2S,5R)-2,5-Dimethylpiperazin-1-yl]-2,6-difluorobenzonitrile

FABMS 252 [M+H]$^+$

Reference Example 6-7

4-[(2S,5R)-2,5-Dimethylpiperazin-1-yl]-phthalonitrile $^1$H-NMR (CDCl$_3$) δ: 1.21 (3H, d), 1.23 (3H, d), 2.73 (1H, dd), 3.11-3.19 (1H, m), 3.29-3.39 (3H, m), 3.73-3.84 (1H, m), 7.00 (1H, dd), 7.09 (1H, d), 7.56 (1H, d)

Reference Example 6-8

4-[(2S,5R)-2,5-Dimethylpiperazin-1-yl]-2-(trifluoromethyl)benzonitrile

FABMS 284 [M+H]$^+$

HPLC retention time: 14.8 min. (the same analytical conditions as in Reference Example 6-1)

Reference Example 7

Methyl (6-trifluoromethyl-pyridin-3-yl]-carbamate

Into 15 ml of pyridine was dissolved 3.00 g of 6-(trifluoromethyl)pyridin-3-amine, and then 2.1 ml of methyl chloroformate was added thereto under ice-cooling, followed by 2 hours of stirring at room temperature. Under ice-cooling, 30 ml of a saturated sodium bicarbonate aqueous solution was added to the reaction solution, followed by 1 hour of stirring. Thereafter, the precipitated crystals were filtrated and, after washing with water, dried under reduced pressure to obtain 3.88 g of the title compound.

$^1$H-NMR (CDCl$_3$) δ: 3.82 (3H, s), 7.39 (1H, br s), 7.65 (1H, d), 8.16-8.22 (1H, m), 8.58-8.63 (1H, m)

Reference Example 8

Alternative Method of Reference Example 7

Into ethyl acetate was suspended 1.91 g of 6-(trifluoromethyl)nicotinic acid, and then 1.52 g of triethylamine and 3.03 g of DPPA were added thereto, followed by 3 hours of stirring. The reaction solution was washed with a saturated sodium bicarbonate aqueous solution and saturated saline and the solvent was removed by evaporation to obtain 2.0 g of 6-(trifluoromethyl)nicotinyl azide as a solid. The resulting acid azide was dissolved into 20 ml of toluene and the solution was heated and refluxed to convert the acid azide into 5-isocyanato-2-(trifluoromethyl)pyridine. Thereafter, 1 ml of methanol was added thereto at room temperature, followed by 1 hour of stirring. The reaction solution was washed with water and then dried over anhydrous magnesium sulfate. Thereafter, the solvent was removed by evaporation to obtain 1.2 g of the title compound.

It is also possible to synthesize the following compounds in the similar manner as in the above Reference Example 7 or 8.

Methyl (6-fluoro-pyridin-3-yl]-carbamate
Methyl (6-bromo-pyridin-3-yl]-carbamate
Methyl (6-cyano-pyridin-3-yl]-carbamate
tert-Butyl (6-cyano-pyridin-3-yl]-carbamate
Ethyl (6-fluoro-pyridin-3-yl]-carbamate
Ethyl (6-bromo-pyridin-3-yl]-carbamate
Ethyl (6-trifluoromethyl-pyridin-3-yl]-carbamate
Phenyl (6-fluoro-pyridin-3-yl]-carbamate
Phenyl (6-bromo-pyridin-3-yl]-carbamate
Phenyl (6-trifluoromethyl-pyridin-3-yl]-carbamate
Phenyl (6-cyano-pyridin-3-yl]-carbamate 4-Nitro-phenyl (6-fluoro-pyridin-3-yl]-carbamate
4-Nitro-phenyl (6-bromo-pyridin-3-yl]-carbamate
4-Nitro-phenyl (6-chloro-pyridin-3-yl]-carbamate
4-Nitro-phenyl (6-trifluoromethyl-pyridin-3-yl]-carbamate
4-Nitro-phenyl (6-cyano-pyridin-3-yl)-carbamate Reference Example 9-1

Ethyl 2-methylpyrimidine-5-carboxylate

Into 25 ml of ether was suspended 762 mg of 60% NaH, and then 20 g of ethyl formate was added dropwise under ice-cooling. Then, 12 ml of an ether solution of 5.0 g of ethyl 3,3-diethoxypropanoate was added dropwise thereto. After 2 days of stirring at the same temperature, 2.50 g of acetamidine hydrochloride was added thereto, followed by 1 day of stirring at room temperature. Then, 5 ml of acetic acid and water were added to the reaction solution, followed by extraction with ethyl acetate. After the organic layer was dried over anhydrous sodium sulfate, the solvent was removed by evaporation and the resulting residue was subjected to silica gel column chromatography to obtain 2.93 g of the title compound from an eluate eluted with ethyl acetate-hexane (3:7, v/v).

$^1$H-NMR (DMSO-$d_6$) δ: 1.34 (3H, t), 2.71 (3H, s), 4.36 (2H, q), 9.12 (2H, s)

The following Reference Examples were synthesized in the similar manner.

Reference Example 9-2

Ethyl 2-tert-butylpyrimidine-5-carboxylate $^1$H-NMR (DMSO-$d_6$) δ: 1.33 (3H, t), 1.38 (9H, s), 4.37 (2H, q), 9.19 (2H, s)

Reference Example 9-3

Ethyl 2-cyclopropylpyrimidine-5-carboxylate $^1$H-NMR (DMSO-$d_6$) δ: 1.04-1.22 (4H, m) 1.33 (3H, t), 2.25-2.36 (1H, m), 4.35 (2H, q), 9.05 (2H, s)

Reference Example 10

4-Fluoro-2-methylbenzonitrile

Into 20 ml of DMF was dissolved 10 g of 1-bromo-4-fluoro-2-methylbenzene, and then 0.2 ml of water was added. Then, 3.72 g of zinc cyanide, 484 mg of 1,1'-bis(diphenylphosphino)ferrocene, and 484 mg of tris(dibenzylideneacetone)dipalladium were added thereto under an argon stream, followed by 2 hours of stirring at 140° C. The reaction solution was ice-cooled, ammonium chloride, aqueous ammonia, and water were added thereto and the resulting solid was collected by filtration. Then, the solid was washed with methanol and the washing liquid was concentrated to obtain 5.7 g of the title compound as a solid.

$^1$H-NMR (DMSO-$d_6$) δ: 2.50 (3H, s), 7.21-7.31 (1H, m), 7.35-7.43 (1H, m), 7.88 (1H, dd)

Reference Example 11

(2R,5S)-4-[4-Cyano-3-(trifluoromethyl)phenyl]-2,5-dimethylpiperadine-1-carbonylchloride Into 30 ml of dichloromethane was dissolved 1.15 g of triphosgen, and then 3.0 g of 4-[(2S,5R)-2,5-dimethylpiperazin-1-yl]-2-trifluoromethylbenzonitrile and a solution of 1.62 ml of triethylamine in 30 ml of dichloromethane were added dropwise thereto under ice-cooling, followed by 1 day of stirring. After washing with water, the organic layer was washed with diluted hydrochloric acid and the solvent was removed by evaporation, the resulting residue was subjected to silica gel column chromatography to obtain 1.44 g of the title compound as a colorless powder from an eluate eluted with hexane-ethyl acetate (1:3, v/v).

$^1$H-NMR (DMSO-$d_6$) δ: 1.07 (1.3H, d), 1.11 (1.7H, d), 1.23 (1.7H, d), 1.25 (1.3H, d), 3.40-3.58 (2H, m), 3.70-3.96 (2H, m), 4.32-3.58 (2H, m), 7.18-7.30 (2H, m), 7.86 (1H, d)

FABMASS 346 [M+H]$^+$

Reference Example 12-1

2-Methylpyrimidine-5-carboxylic acid

In 30 ml of ethanol and 20 ml of a 1M sodium hydroxide aqueous solution, 2.9 g of ethyl 2-methylpyrimidine-5-carboxylate was stirred for 2 hours. The solvent was removed by evaporation and an appropriate amount of water and diethyl ether were added thereto, followed by liquid-separating operation. The resulting aqueous layer was made weakly acidic with a 1M hydrochloric acid aqueous solution and then the resulting crystals were collected by filtration, washed with water, and then dried to obtain 1.9 g of the title compound.

FABMASS 139 [M+H]$^+$

The following Reference Examples were synthesized in the similar manner.

Reference Example 12-2

2-tert-Butylpyrimidine-5-carboxylic acid

FABMASS 181 [M+H]$^+$

Reference Example 12-3

2-Cyclopropylpyrimidine-5-carboxylic acid

FABMASS 165 [M+H]$^+$

Reference Example 13-1

2-Cyclopropylquinazoline-6-carbonitrile

Into 60 ml of acetonitrile were suspended 1.5 g of 4-fluoro-3-formylbenzonitrile, 2.0 g of potassium carbonate, 2.3 g of molecular sieves 4A, and 1.7 g of cyclopropanecarboxyimidamide hydrochloride, followed by 6 days of heating under refluxing. Insoluble matter was separated by filtration and the filtrate was concentrated. The residue was subjected to silica gel column chromatography to obtain 220 mg of the title compound from an eluate eluted with hexane-ethyl acetate (8:2, v/v).

FABMASS 196 [M+H]$^+$

Reference Example 13-2

Using acetamidine hydrochloride, 2-methylqunazoline-6-carbonitrile was synthesized by the similar operations as in Reference Example 13-1.
FABMASS 170 [M+H]+

Reference Example 14-1

2-Cyclopropylquinazoline-6-carboxylic acid

Into 8 ml of 2-propanol and 1 ml of water were dissolved 210 mg of 2-cyclopropylquinazoline-6-carbonitrile and 450 mg of potassium hydroxide, followed by heating under refluxing overnight. Hydrochloric acid was added thereto and the solvent was removed by evaporation to obtain the title compound as a crude carboxylic acid.
FABMASS 215 [M+H]+

Reference Example 14-2

2-Methylquinazoline-6-carboxylic acid was synthesized in the similar manner as in Reference Example 14-1.
FABMASS 189 [M+H]+

Reference Example 15

2-Methoxy-6-nitroquinoxaline

Into 10 ml of THF was dissolved 1.16 g of 2-chloro-6-nitroquinoxaline, and then 1.0 g of sodium methoxide was added thereto, followed by heating under refluxing for 30 minutes. Then, the solvent was removed by evaporation. Water was added to the residue, followed by extraction with ethyl acetate. The organic layer was washed with saturated saline. After the solvent was removed by evaporation, the residue was crystallized from diethyl ether-hexane to obtain 776 mg of the title compound.
FABMASS 206 [M+H]+

Reference Example 16

2-Morpholino-6-nitroquinoxaline

Into 10 ml of THF was dissolved 1.16 g of 2-chloro-6-nitroquinoxaline, and then 20 ml of morpholine was added thereto, followed by heating under refluxing for 30 minutes. Then, the solvent was removed by evaporation. Water was added to the residue, followed by extraction with ethyl acetate. The organic layer was washed with a saturated sodium bicarbonate aqueous solution and saturated saline. After the solvent was removed by evaporation, the residue was crystallized from diethyl ether to obtain 1.5 g of the title compound.
FABMASS 261 [M+H]+

Reference Example 17-1

2-Methoxyquinoxalin-6-amine

Into 20 ml of methanol was dissolved 726 mg of 2-methoxy-6-nitroquinoxaline, and then 1.0 g of iron powder and a saturated ammonium chloride aqueous solution were added thereto, followed by heating under refluxing overnight. Insoluble matter was separated by filtration using celite and then the solvent was removed by evaporation. A sodium bicarbonate aqueous solution was added to the residue, followed by extraction with ethyl acetate. After the organic layer was dried over anhydrous magnesium sulfate, the solvent was removed by evaporation and the resulting residue was purified by silica gel column chromatography to obtain 770 mg of the title compound from chloroform-methanol (100:1, v/v).
FABMASS 176 [M+H]+

Reference Example 17-2

2-Morpholinoquinoxalin-6-amine was obtained in the similar manner as in Reference Example 17-1.
FABMASS 231 [M+H]+

Reference Example 17-3

2-Morpholinoquinolin-6-amine was obtained by reducing 2-morpholino-6-nitroquinoline in the similar manner as in Reference Example 17-1.
FABMASS 230 [M+H]+

Reference Example 18

Imidazo[1,2-a]pyridine-7-carboxylic acid

In 10 ml of methanol was dissolved 866 mg of methyl imidazo[1,2-a]pyridine-7-carboxylate, and then 5 ml of a 1M sodium hydroxide aqueous solution was added thereto, followed by stirring overnight. Then, 5 ml of 1M hydrochloric acid was added thereto and the solvent was removed by evaporation. A small amount of water, ethanol, and methanol were added thereto and crystals were collected by filtration to obtain 530 mg of the title compound.
FABMASS 163 [M+H]+

Example 1-1

(2R,5S)-4'-Cyano-4-(4-cyano-3-fluoro-5-methoxyphenyl)-2,5-dimethylpiperazine-1-carboxanilide Into 20 ml of acetonitrile was dissolved 500 mg of 4-[(2S,5R)-2,5-dimethylpiperazin-1-yl]-2-fluoro-6-methoxybenzonitrile, and then 274 mg of 4-isocyanatobenzonitrile was added thereto, followed by 1 hour of stirring at room temperature. The reaction solution was concentrated, followed by addition of ethyl acetate and filtration. The filtrate was removed by evaporation and the resulting powder was crystallized from hexane-ethyl acetate (85:15, v/v) to obtain 535 mg of the title compound.

Example 2-1

(2R,5S)-4-(4-Cyano-3,5-difluorophenyl)-N-(2-fluoro-4-pyridyl)-2,5-dimethylpiperazine-1-carboxamide Into 20 ml of ethyl acetate was suspended 875 mg of 2-fluoroisonicotinic acid, and then 0.76 ml of oxalyl chloride and 0.01 ml of DMF were added thereto, followed by 30 minutes of stirring at room temperature. After the solvent was removed by evaporation, ethyl acetate was added again and the solvent was removed by evaporation. The resulting 2-fluoroisonicotinyl chloride was dissolved in 20 ml of ethyl acetate, and then 1.01 g of sodium azide was added thereto under ice-cooling, followed by 2 hours of stirring at room temperature. The organic layer was washed with a saturated sodium bicarbonate aqueous solution and then water. After the layer was dried over anhydrous sodium sulfate, the solvent was removed by evaporation. Toluene was added thereto and the solvent was removed again by evaporation to obtain 2-fluoroisonicotinyl azide. The resulting acid azide was heated and refluxed in 30 ml of toluene for 30 minutes to convert it into 2-fluoro-4-isocyanatopyridine, followed by ice-cooling.

Into 5 ml of ethyl acetate was dissolved 1.09 g of 4-[(2S,5R)-2,5-dimethylpiperazin-1-yl]-2,6-difluorobenzonitrile, and the resulting solution was added dropwise to the above reaction solution, followed by 18 hours of stirring at room temperature. The crystals formed were collected by filtration and then washed with ethyl acetate to obtain 1.01 g of the title compound as colorless crystals.

Example 3-1

(2R,5S)-4-(4-Cyano-3-fluoro-5-methoxyphenyl)-N-(2-cyclopropylpyrimidine-5-yl)-2,5-dimethylpiperazine-1-carboxamide Into 10 ml of ethyl acetate was suspended 374 mg of 2-cyclopropylpyrimidine-5-carboxylic acid, and then 345 mg of triethylamine and 690 mg of DPPA were added thereto, followed by 2 hours of stirring at room temperature. The reaction solution was washed with a saturated sodium bicarbonate aqueous solution and then water. After the solution was dried over anhydrous sodium sulfate, the solvent was removed by evaporation. Toluene was added thereto and the solvent was removed by evaporation to obtain 2-cyclopropylpyrimidine-5-carboxyl azide. The resulting acid azide was dissolved into 20 ml of toluene and the solution was heated and refluxed for 30 minutes to convert the acid azide into 2-cyclopropyl-5-isocyanatopyridine, followed by ice-cooling of the reaction solution. Into 3 ml of ethyl acetate was dissolved 500 mg of 4-[(2S,5R)-2,5-dimethylpiperazin-1-yl]-2-fluoro-6-methoxybenzonitrile, and the resulting solution was added dropwise to the above reaction solution, followed by 18 hours of stirring at room temperature. The reaction solution was evaporated and the resulting residue was subjected to silica gel column chromatography and a resulting oily product from an eluate using methanol-chloroform (3:97, v/v) was crystallized from ethyl acetate-diethyl ether to obtain 626 mg of the title compound.

Example 4-1

(2R,5S)-4'-(1-Cyanocyclopropyl)-4-(4-cyano-3-fluoro-5-methoxyphenyl)-2,5-dimethylpiperazine-1-carboxanilide Into 10 ml of pyridine was dissolved 475 mg of 1-(4-aminophenyl)cyclopropanecarbonitrile, and then 493 mg of chloro phenyl carbonate was added thereto under ice-cooling, followed by 24 hours of stirring at room temperature. Then, 5 ml of a pyridine solution of 790 mg of 4-[(2S,5R)-2,5-dimethylpiperazin-1-yl]-2-fluoro-6-methoxybenzonitrile was added dropwise thereto, followed by 1 hour of stirring at 100° C. After the reaction solution was evaporated and the resulting residue was dissolved in ethyl acetate, the solution was washed with a saturated sodium bicarbonate aqueous solution and then water. After the solution was dried over anhydrous sodium sulfate, the solvent was removed by evaporation. The residue was subjected to silica gel column chromatography to obtain 751 mg of the title compound from an eluate using ethyl acetate-hexane (1:1, v/v).

Example 5

(2R,5S)-4'-Cyano-4-(4-cyano-3-trifluoromethylphenyl)-2,5-dimethyl-2'-trifluoromethoxypiperazine-1-carboxanilide Into 10 ml of DMF was suspended 185 mg of 60% NaH, and then 855 mg of 4-amino-3-(trifluoromethoxy)benzonitrile was added thereto, followed by 10 minutes of stirring at 50° C.

Into 30 ml of DMF was dissolved 1.33 g of (2R,5S)-4-[4-cyano-3-(trifluoromethyl)phenyl]-2,5-dimethylpiperazine-1-carbonyl chloride, and the above reaction solution was added dropwise thereto at room temperature, followed by 3 hours of stirring. Water was added to the reaction solution, followed by extraction with ethyl acetate. After the organic layer was washed with water, the solvent was removed by evaporation. The resulting residue was subjected to silica gel column chromatography to obtain 1.08 g of the title compound from an eluate using hexane-ethyl acetate (1:1, v/v).

Example 6-1

(2R,5S)-2'-Cyano-4-(4-cyano-3-methoxyphenyl)-2,5-dimethyl-5'-trifluoromethylpiperazine-1-carboxanilide Into 10 ml of THF was suspended 80 mg of 60% NaH, and then 337 mg of 2-amino-4-trifluoromethylbenzonitrile was added thereto at room temperature, followed by 30 minutes of stirring at room temperature. Then, 558 mg of (2R,5S)-4-[4-cyano-3-(trifluoromethyl)phenyl]-2,5-dimethylpiperazine-1-carbonyl chloride was added thereto, followed by 17 hours of stirring at room temperature. Water was added to the reaction solution, followed by extraction with chloroform. After the organic layer was washed with water, the solvent was removed by evaporation. The resulting residue was subjected to silica gel column chromatography to obtain 358 mg of the title compound from an eluate using hexane-ethyl acetate (1:1, v/v).

Example 7-1

(2R,5S)-4-(4-Cyano-3-methoxyphenyl)-2,5-dimethyl-N-(6-trifluoromethyl-3-pyridyl)piperazine-1-carboxamide Into 5 ml of toluene were dissolved 500 mg of methyl 6-(trifluoromethyl)pyridin-3-ylcarbamate and 557 mg of 4-[(2S,5R)-2,5-dimethylpiperazin-1-yl]-2-methoxybenzonitrile, and then 0.03 ml of DBU was added thereto, followed by heating to 100° C. and 8 hours of stirring. The reaction solution was concentrated and the residue was subjected to silica gel column chromatography to obtain 450 mg of the title compound from an eluate using chloroform-methanol (96:4, v/v).

The following table shows structures and values of physical properties of the compounds synthesized in the above Examples and in the similar manner as in the above Examples.

In this connection, the symbols in the table have the following meanings.

Ex.: Example No., Me: methyl, and MS: this symbol means a value of FABMS [M+H]$^+$ unless otherwise specifically indicated. mp: melting point (° C.), recrystallization solvent was shown in parenthesis and the value exhibiting decomposition was described with (dec.). HPLC: HPLC retention time (column: CHIRALCEL OJ-H manufactured by Daicel Chemical Industries, Ltd., size: 4.6 cm×250 mm, mobile phase: hexane:ethanol (8:2), flow rate: 0.5 ml/min., temperature: 40° C., wavelength: 254 nm).

TABLE 1

| Ex. | R1 | R2 | Cy. Salt | Physical data |
|---|---|---|---|---|
| 1-1 | OMe | F | 4-CN-phenyl | MS: 408 |
| 1-2 | Cl | H | 4-CN-phenyl | MS: 394 |
| 1-3 | OMe | H | 4-CN-phenyl | MS: 390 |
| 1-4 | Br | H | 4-CN-phenyl | MS: 438 |
| 1-5 | OMe | F | 4-acetyl-phenyl | MS: 425 |
| 1-6 | Cl | H | 4-acetyl-phenyl | MS: 411 |
| 1-7 | OMe | H | 4-acetyl-phenyl | MS: 407 |
| 1-8 | OMe | F | 4-CF₃-phenyl | MS: 451 |
| 1-9 | OMe | H | 4-SCF₃-phenyl | MS: 465 |
| 1-10 | OMe | H | 4-OCF₃-phenyl | MS: 449 |
| 1-11 | OMe | H | 3-OMe-phenyl | MS: 395 |
| 1-12 | OMe | H | 4-NO₂-phenyl | MS: 410 |
| 1-13 | CN | H | 4-CN-phenyl | MS: 385 |

TABLE 1-continued
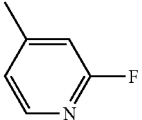
| Ex. | R1 | R2 | Cy. Salt | Physical data |
|---|---|---|---|---|
| 2-1 | F | F | 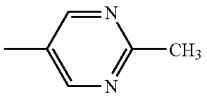 | mp: 278-280 (dec.) (AcOEt) |
| 2-2 | CF3 | H | 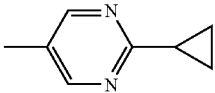 | MS: 419 |
| 3-1 | OMe | F | 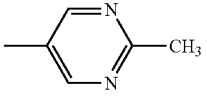 | MS: 425 |
| 3-2 | OMe | F | 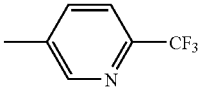 | MS: 399 |
| 3-3 | OMe | F | 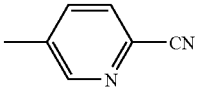 | mp: 217-220 (AcOEt) MS: 452 |
| 3-4 | OMe | F | 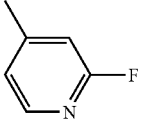 | MS: 409 |
| 3-5 | OMe | F | 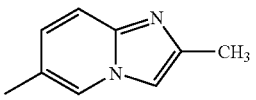 | MS: 402 |
| 3-6 | OMe | F | 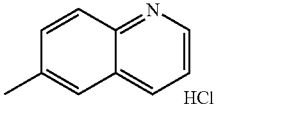 | MS: 437 |
| 3-7 | OMe | F | 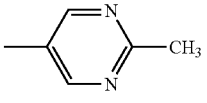 HCl | mp: 184-190 (dec.) (MeOH—Et$_2$O) |
| 3-8 | Cl | H | 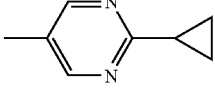 | MS: 385 |
| 3-9 | Cl | H | 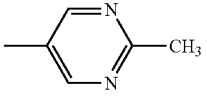 | MS: 411 |

TABLE 1-continued
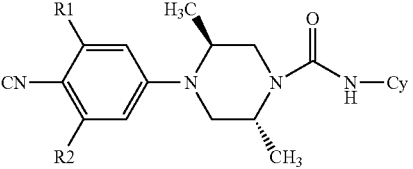
| Ex. | R1 | R2 | Cy. Salt | Physical data |
|---|---|---|---|---|
| 3-10 | Cl | H | 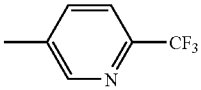 | MS: 468 |
| 3-11 | Cl | H | 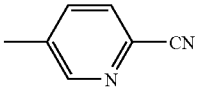 | mp: 222-224 (AcOEt—EtOH) |
| 3-12 | Cl | H | 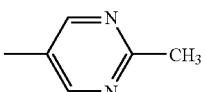 | MS: 395 |
| 3-13 | OMe | H | 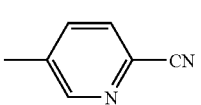 | MS: 381 |
| 3-14 | OMe | H | 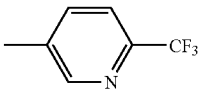 | MS: 391 |
| 3-15 | OMe | H | 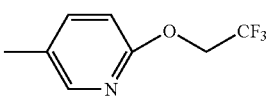 | mp: 211-212 (AcOEt) |
| 3-16 | OMe | H | 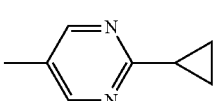 | MS: 464 |
| 3-17 | OMe | H | 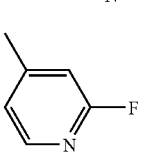 | MS: 407 |
| 3-18 | OMe | H | 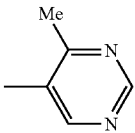 | MS: 384 |
| 3-19 | OMe | H | 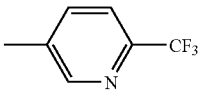 | MS: 381 |
| 3-20 | F | H | 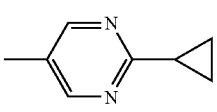 | mp: 175-176 (AcOEt-hexane) MS: 422 |
| 3-21 | Br | H |  | mp: 98-101 (Et2O) |

TABLE 1-continued

| Ex. | R1 | R2 | Cy. Salt | Physical data |
|---|---|---|---|---|
| 3-22 | Br | H | 2-methyl-pyrimidin-5-yl | mp: 116-118 |
| 3-23 | Br | H | 6-(trifluoromethyl)pyridin-3-yl | mp: 216-218 (AcOEt-hexane) HPLC: 24.9 min |
| 3-24 | Br | H | 6-cyanopyridin-3-yl | MS: 439 |
| 3-25 | Br | H | isoquinolin-6-yl | MS: 464 |
| 3-26 | Br | H | 2-fluoro-4-methylpyridin-4-yl | MS: 432 |
| 3-27 | Br | H | 2-chloro-4-methylpyridin-4-yl | MS: 448 |
| 3-28 | Me | H | 6-(trifluoromethyl)pyridin-3-yl | mp: 220-223 (toluene-AcOEt) |
| 3-29 | O-tBu | H | 6-(trifluoromethyl)pyridin-3-yl | MS: 476 |
| 3-30 | CF3 | H | 2-cyclopropylpyrimidin-5-yl | MS: 445 |
| 3-31 | CF3 | H | 2-tert-butylpyrimidin-5-yl | MS: 461 |
| 3-32 | CF3 | H | imidazo[1,2-a]pyridin-6-yl HCl | MS: 443 |
| 3-33 | CF3 | H | benzo[1,2,3]thiadiazol-6-yl | MS: 461 |

TABLE 1-continued

| Ex. | R1 | R2 | Cy. Salt | Physical data |
|---|---|---|---|---|
| 3-34 | CF3 | H | imidazo[1,2-a]pyridinyl · HCl | MS: 443 |
| 3-35 | CF3 | H | 2-methylquinazolinyl | MS: 469 |
| 3-36 | CF3 | H | 2-cyclopropylquinazolinyl | MS: 495 |
| 3-37 | CF3 | H | indanonyl | MS: 457 |
| 3-38 | CF3 | H | quinoxalinyl | FABMS 453 [M − H]− |
| 3-39 | OMe | OMe | 6-(trifluoromethyl)pyridin-3-yl | MS: 464 |
| 3-40 | CN | H | 6-(trifluoromethyl)pyridin-3-yl | MS: 429 |
| 3-41 | CN | H | 2-methylpyrimidin-5-yl | MS: 376 |
| 3-42 | CN | H | 2-cyclopropylpyrimidin-5-yl | MS: 402 |
| 4-1 | F | OMe | 4-(1-cyanocyclopropyl)phenyl | MS: 448 |
| 4-2 | CF3 | H | benzothiazolyl | MS: 460 |

TABLE 1-continued

| Ex. | R1 | R2 | Cy. Salt | Physical data |
|---|---|---|---|---|
| 4-3 | CF3 | H | (5-methyl-isobenzofuran-1(3H)-one) | MS: 459 |
| 4-4 | CF3 | H | (6-methyl-2-methylbenzothiazole) HCl | MS: 474 |
| 4-5 | CF3 | H | (6-methyl-2-morpholinoquinoline) | MS: 539 |
| 4-6 | CF3 | H | (6-methyl-3-methoxyquinoxaline) | MS: 485 |
| 4-7 | CF3 | H | (6-methyl-3-morpholinoquinoxaline) | MS: 540 |
| 4-8 | CF3 | H | (6-methyl-3,4-dihydronaphthalen-1(2H)-one) | MS: 471 |
| 4-9 | OMe | F | (6-methyl-2-methylbenzothiazole) HCl | MS: 454 |
| 4-10 | OMe | F | (5-methyl-isobenzofuran-1(3H)-one) | MS: 439 |
| 4-11 | OMe | H | (2-chloro-4-methylbenzonitrile) | MS: 424 |

TABLE 1-continued

| Ex. | R1 | R2 | Cy. Salt | Physical data |
|---|---|---|---|---|
| 4-12 | OMe | H | 2-methyl-4-chloro-benzonitrile group | MS: 424 |
| 4-13 | OMe | H | 4-methyl-2-trifluoromethyl-benzonitrile group | MS: 458 |
| 4-14 | OMe | H | 3-methyl-2-chloro-benzonitrile group | MS: 424 |
| 4-15 | OMe | H | 2,6-dimethyl-benzonitrile group | MS: 404 |
| 4-16 | OMe | H | 6-methylquinoxaline group | FABMS 415 [M − H]− |
| 4-17 | OMe | H | 2,6-dimethylquinoline group | MS: 430 |
| 4-18 | OMe | H | 2-methyl-4-methyl-benzonitrile group | MS: 404 |
| 4-19 | OMe | H | 3,4-dimethyl-benzonitrile group | MS: 404 |
| 4-20 | OMe | H | 2,5-dimethyl-benzonitrile group | MS: 404 |
| 4-21 | OMe | H | 3,4-dimethyl-benzonitrile group | MS: 404 |

TABLE 1-continued

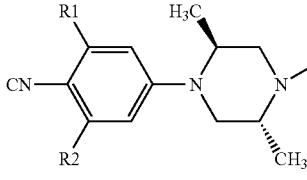

| Ex. | R1 | R2 | Cy. Salt | Physical data |
|---|---|---|---|---|
| 4-22 | OMe | H | 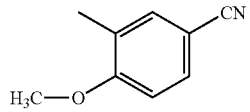 | MS: 450 |
| 4-23 | OMe | H | 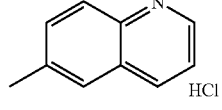 | MS: 420 |
| 4-24 | OMe | H | 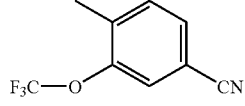 HCl | MS: 416 |
| 5 | CF3 | H | 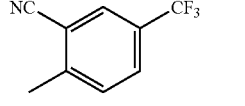 | MS: 512 |
| 6-1 | OMe | H | 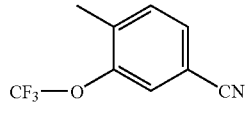 | MS: 458 |
| 6-2 | OMe | H | 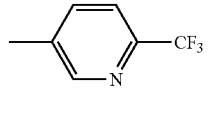 | MS: 474 |
| 7-1 | OMe | H | 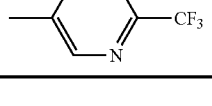 | MS: 434 |
| 7-2 | Br | H | 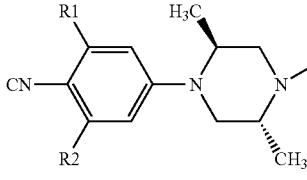 | MS: 483 |

Moreover, NMR values of the above Examples were shown in the following table.

TABLE 2

| Ex. | $^1$H-NMR(DMSO-$d_6$) δ: |
|---|---|
| 1-3 | 1.07 (3H, d), 1.20 (3H, d), 3.28-3.38 (4H, m), 3.61 (1H, d), 4.29 (1H, br s), 4.50 (1H, br s), 6.53 (1H, d), 6.60 (1H, dd), 7.44 (1H, d), 7.70 (4H, s), 9.03 (1H, s) |
| 1-5 | 1.11 (3H, d), 1.19 (3H, d), 2.51 (3H, s), 3.33-3.45 (2H, m), 3.68 (1H, d), 3.88 (1H, d), 3.92 (3H, s), 4.31 (1H, br s), 4.51 (1H, br s), 6.36 (1H, d), 6.61 (1H, dd), 7.65 (2H, d), 7.88 (2H, d), 8.95 (1H, s) |
| 1-6 | 1.09 (3H, d), 1.18 (3H, d), 2.51 (3H, s), 3.29-3.45 (2H, m), 3.67 (1H, d), 3.89 (1H, d), 4.29 (1H, br s), 4.51 (1H, br s), 7.00 (1H, dd), 7.17 (1H, d), 7.66 (2H, d), 7.89 (2H, d), 8.94 (1H, s) |

TABLE 2-continued

| Ex. | $^1$H-NMR(DMSO-$d_6$) δ: |
|---|---|
| 1-7 | 1.08 (3H, d), 1.20 (3H, d), 2.51 (3H, s), 3.28-3.48 (2H, m), 3.62 (1H, d), 3.85-3.94 (4H, m), 4.29 (1H, br s), 4.52 (1H, br s), 6.54 (1H, s), 6.60 (1H, d), 7.44 (1H, d), 7.65 (2H, d), 7.88 (2H, d), 9.39 (1H, s) |
| 1-13 | 1.09 (3H, d), 1.18 (3H, d), 3.28-3.48 (2H, m), 3.75 (1H, d), 3.89 (1H, d), 4.33 (1H, br s), 4.51 (1H, br s), 7.30 (1H, dd), 7.61 (1H, d), 7.82 (1H, d), 9.02 (1H, s) |
| 2-1 | 1.10 (3H, d), 1.17 (3H, d), 3.30-3.47 (2H, m), 3.67-3.77 (1H, m), 3.83-3.94 (1H, m), 4.24-4.35 (1H, m), 4.43-4.56 (1H, m), 6.92 (2H, d), 7.28-7.45 (2H, m), 8.00 (1H, d), 9.27 (1H, br s) |
| 2-2 | 1.11 (3H, d), 1.20 (3H, d), 2.54 (3H, s), 3.30-3.50 (2H, m), 3.68-3.81 (1H, m), 3.83-3.95 (1H, m), 4.32-4.55 (2H, m), 7.23-7.35 (2H, m), 7.86 (1H), 8.79 (2H, s), 8.83 (1H, br s) |

TABLE 2-continued

| Ex. | ¹H-NMR(DMSO-d$_6$) δ: |
|---|---|
| 3-1 | 0.89-1.01 (4H, m), 1.10 (3H, d), 1.18 (3H, d), 2.08-2.18 (1H, m), 3.27-3.45 (2H, m), 3.64-3.74 (1H, m), 3.81-3.89 (1H, m), 3.92 (3H, s), 4.26-4.37 (1H, m), 4.40-4.51 (1H, m), 6.34-6.39 (1H, m), 6.57-6.65 (1H, m), 8.71 (2H, s), 8.78 (1H, br s) |
| 3-4 | 1.11 (3H, d), 1.21 (3H, d), 3.28-3.49 (2H, m), 3.70 (1H, d), 3.86-3.95 (4H, m), 4.33 (1H, br s), 4.50 (1H, br s), 6.37 (1H, br s), 6.61 (1H, dd), 7.91 (1H, d), 8.15 (1H, dd8), 8.85 (1H, d), 9.25 (1H, s) |
| 3-5 | 1.09 (3H, d), 1.19 (3H, d), 3.30-3.48 (2H, m), 3.64-3.94 (5H, m), 4.32 (1H, br s), 4.49 (1H, br s), 6.37 (1H, d), 6.61 (1H, dd), 7.32 (1H, d), 7.40 (1H, dt), 8.00 (1H, d, J=6), 9.29 (1H, s) |
| 3-7 | 1.13 (3H, d), 1.23 (3H, d), 3.33-3.52 (2H, m), 3.66-3.76 (1H, m), 3.93 (3H, s), 3.97-4.05 (1H, m), 4.29-4.40 (1H, m), 4.55-4.65 (1H, m), 6.36-6.41 (1H, m), 6.58-6.66 (1H, m), 7.94 (1H, dd), 8.25-8.29 (2H, m), 8.51 (1H, br s), 8.93-9.00 (1H, m), 9.06 (1H, dd), 9.45 (1H, br s) |
| 3-8 | 1.09 (3H, d), 1.19 (3H, d), 2.54 (3H, s), 3.30-3.43 (2H, m), 3.68 (1H, d), 3.87 (1H, d), 4.25-4.35 (1H, m), 4.42-4.52 (1H, m), 7.01 (1H, dd), 7.18 (1H, d), 7.67 (1H, d, J=9), 8.79 (2H, s) |
| 3-9 | 0.85-1.05 (4H, m), 1.09 (3H, d), 1.18 (3H, d), 2.06-2.20 (1H, m), 3.26-3.46 (2H, m), 3.68 (1H, d), 3.86 (1H, d), 4.30 (1H, br s), 4.47 (1H, br s), 7.01 (1H, dd), 7.18 (1H,), 7.67 (1H, d), 8.72 (2H, s), 8.78 (1H, s) |
| 3-12 | 1.09 (3H, d, J=7), 1.20 (3H, d, J=6), 3.33-3.50 (2H, m), 3.69 (1H, d, J=13), 3.90 (1H, d, J=14), 4.31 (1H, br s), 4.51 (1H, br s), 7.01 (1H, dd, J=2, 9), 7.18 (1H, d, J=2), 7.68 (1H, d, J=9), 7.91 (1H, d), 8.16 (1H, dd), 8.85 (1H, d), 9.25 (1H, s) |
| 3-14 | 1.08 (3H, d), 1.23 (3H, d), 3.30-3.95 (7H, m), 4.31 (1H, br s), 4.51 (1H, br s), 6.54 (1H, d), 6.61 (1H, dd), 7.45 (1H, d, J=9), 7.91 (1H, d), 8.15 (1H, dd), 8.85 (1H, d), 9.25 (1H, s) |
| 3-15 | 1.09 (3H, d), 1.23 (3H, d), 3.30-3.40 (1H, m), 3.42-3.52 (1H, m), 3.60-3.68 (1H, m), 3.86-3.96 (1H, m), 3.90 (3H, s), 4.24-4.38 (1H, m), 4.44-4.60 (1H, m), 6.50-6.66 (2H, m), 7.44 (1H, d), 7.79 (1H, d), 8.19 (1H, dd), 8.86 (1H, d), 9.16 (1H, br s) |
| 3-17 | 0.85-1.02 (4H, m), 1.08 (3H, d, J=6), 1.20 (3H, d), 2.08-2.20 (1H, m), 3.26-3.50 (2H, m), 3.58-3.67 (1H, m), 3.83-3.94 (1H, m), 3.85 (3H, m), 4.30 (1H, br s), 4.47 (1H, br s), 6.54 (1H, br s), 6.56-6.68 (1H, m), 7.44 (1H, d), 8.72 (2H, s), 8.79 (1H, br s) |
| 3-18 | 1.08 (3H, d), 1.22 (3H, d), 3.30-3.50 (2H, m), 3.57-3.93 (5H, m), 4.31 (1H, br s), 4.51 (1H, br s), 6.54 (1H, d), 6.61 (1H, dd), 7.34 (1H, d), 7.38-7.43 (1H, m), 7.45 (1H, d), 8.00 (1H, d), 9.29 (1H, s) |
| 3-21 | 0.89-1.00 (4H, m), 1.09 (3H, d), 1.18 (3H, d), 2.09-2.17 (1H, m), 3.28-3.44 (2H, m), 3.67 (1H, d), 3.86 (1H, d), 4.29 (1H, br s), 4.46 (1H, br s), 7.04 (1H, dd), 7.30 (1H, d), 7.64 (1H, d), 8.72 (2H, s), 8.78 (1H, s) |
| 3-23 | 1.09 (3H, d), 1.20 (3H, d), 3.30-3.38 (1H, m), 3.40-3.49 (1H, m), 3.63-3.72 (1H, m), 3.86-3.99 (1H, m), 4.25-4.35 (1H, m), 4.45-4.56 (1H, m), 7.01-7.07 (1H, m), 7.28-7.32 (1H, m), 7.65 (1H, d), 7.79 (1H, d), 8.15-8.22 (1H, m), 8.82-8.87 (1H, m), 9.15 (1H, s) |
| 3-26 | 1.07 (3H, d), 1.19 (3H, d), 3.29-3.37 (1H, m), 3.38-3.47 (1H, m), 3.61-3.72 (1H, m), 3.83-3.92 (1H, m), 4.23-4.34 (1H, m), 4.44-4.54 (1H, m), 7.03 (1H, dd), 7.26-7.34 (1H, m), 7.37-7.42 (1H, m), 7.64 (1H, d), 8.00 (1H, d), 9.27 (1H, br s) |
| 3-27 | 1.07 (3H, d), 1.19 (3H, d), 3.28-3.37 (1H, m), 3.38-3.47 (1H, m), 3.61-3.72 (1H, m), 3.83-3.92 (1H, m), 4.23-4.34 (1H, m), 4.43-4.53 (1H, m), 7.03 (1H, dd), 7.29 (1H, d), 7.49 (1H, d), 7.64 (1H, d), 7.67 (1H, d), 8.16 (1H, d), 9.19 (1H, br s) |
| 3-28 | 1.07 (3H, d), 1.22 (3H, d), 2.40 (3H, s), 3.26-3.35 (1H, m), 3.40-3.49 (1H, m), 3.56-3.64 (1H, m), 3.87-3.96 (1H, m), 4.22-4.32 (1H, m), 4.43-4.57 (1H, m), 6.84-6.90 (1H, m), 6.92-6.97 (1H, m), 7.52 (1H, d), 7.79 (1H, d), 8.16-8.23 (1H, m), 8.83-8.87 (1H, m), 9.16 (1H, s) |
| 3-30 | 0.88-1.01 (4H, m), 1.11 (3H, d), 1.20 (3H, d), 2.08-2.18 (1H, m), 3.35-3.49 (2H, m), 3.70-3.79 (1H, m), 3.83-3.93 (1H, m), 4.33-4.55 (2H, m), 7.24-7.33 (2H, m), 7.85 (1H, d), 8.72 (2H, s), 8.79 (1H, br s) |
| 3-31 | 1.11 (3H, d), 1.20 (3H, d), 1.33 (9H, s), 3.35-3.50 (2H, m), 3.70-3.79 (1H, m), 3.84-3.93 (1H, m), 4.33-4.55 (2H, m), 7.24-7.33 (2H, m), 7.85 (1H, d, J=9), 8.82 (2H, s), 8.86 (1H, br s) |
| 3-32 | 1.14 (3H, d), 1.23 (3H, d), 3.35-3.55 (2H, m), 3.73-3.82 (1H, m), 4.07-4.18 (1H, m), 4.35-4.45 (1H, m), 4.61-4.72 (1H, m), 7.26-7.35 (2H, m), 7.86 (1H, d), 7.94 (1H, d), 8.14 (1H, d), 8.22-8.28 (1H, m), 8.42 (1H, d), 9.42 (1H, br s), 9.59 (1H, br s), 14.7 (1H, br s) |
| 3-36 | 1.00-1.28 (10H, m), 2.23-2.36 (1H, m), 3.36-3.52 (2H, m), 3.76 (1H, d), 3.95 (1H, d), 4.32-4.46 (1H, m), 4.47-4.64 (1H, m), 7.20-7.37 (2H, m), 7.78 (1H, d), 7.86 (1H, d), 8.02 (1H, dd), 8.21 (1H, d), 9.00 (1H, s), 9.33 (1H, s) |
| 3-37 | 1.10 (3H, d), 1.20 (3H, d), 2.54-2.60 (2H, m), 3.00-3.07 (2H, m), 3.35-3.50 (2H, m), 3.69-3.78 (1H, m), 3.86-3.95 (1H, m), 4.31-4.41 (1H, m), 4.48-4.58 (1H, m), 7.26 (1H, dd), 7.30 (1H, d), 7.49 (1H, dd), 7.53 (1H, d), 7.76 (1H, br s), 7.85 (1H, d, J=9), 9.00 (1H, br s) |
| 3-38 | 1.14 (3H, d), 1.20 (3H, d), 3.38-3.64 (2H, m), 3.77 (1H, d), 3.97 (1H, d), 4.40 (1H, br s), 4.59 (1H, br s), 7.25-7.35 (2H, m), 7.86 (1H, d), 7.96-8.05 (2H, m), 8.29 (1H, d), 8.77 (1H, d), 8.84 (1H, d), 9.13 (1H, s) |
| 4-1 | 1.09 (3H, d), 1.16 (3H, d), 1.38-1.45 (2H, m), 1.64-1.71 (2H, m), 3.28-3.43 (2H, m), 3.62-3.70 (1H, m), 3.80-3.90 (1H, m), 3.92 (3H, s), 4.24-4.34 (1H, m), 4.42-4.52 (1H, m), 6.36 (1H, br s), 6.55-6.64 (1H, m), 7.22 (1H, d), 7.50 (1H, d), 8.64 (1H, s) |
| 4-3 | 1.11 (3H, d), 1.21 (3H, d), 3.34-3.51 (2H, m), 3.68-3.80 (1H, m), 3.86-3.97 (1H, m), 4.30-4.44 (1H, m), 4.47-4.60 (1H, m), 5.34 (2H, s), 7.22-7.34 (2H, m), 7.62 (1H, dd), 7.77 (1H, d), 7.80-7.92 (2H, m), 9.12 (1H, s) |
| 4-5 | 1.13 (3H, d), 1.20 (3H, d), 3.36-3.62 (5H, m), 3.71-3.77 (5H, m), 3.86 (1H, d), 3.93 (1H, d), 4.37 (1H, br s), 4.55 (1H, br s), 7.18 (1H, d), 7.27 (1H, d), 7.31 (1H, s), 7.51 (1H, d), 7.65 (1H, d), 7.76-7.78 (2H, m), 7.98 (1H, d), 8.68 (1H, s) |
| 5 | 1.10 (3H, d, J=7), 1.20 (3H, d), 3.36-3.53 (2H, m), 3.68-3.85 (2H, m), 4.30-4.53 (2H, m), 7.21-7.33 (2H, m), 7.78-7.82 (2H, m), 7.85 (1H, d), 7.94-7.98 (1H, m), 8.88 (1H, br s) |

(Test Methods)

The usefulness of the compounds of the present invention can be confirmed by the following test methods.

1. Transcription Activation Regulatory Action Toward Human Androgen Receptor

Acquisition of Human Androgen Receptor-Expressing, Stable Transformant of MMTV Reporter Gene, and Stable Transformant of SV40 Reporter Gene CHO cells were seeded on a dish for cell culture having a diameter of 100 mm in an amount of $1 \times 10^6$ cells. After 12 to 18 hours, a human androgen receptor-expressing plasmid, MMTV-LTR luciferase reporter plasmid (also inclusive of neomycin resistant gene) co-precipitated with calcium phosphate was added thereto to effect transfection. After 15 hours, the medium was removed and the cells were diluted to several cell concentrations and seeded again respectively, and GENETICIN (registered trademark) (neomycin) was added to the medium so as to be a final concentration of 500 μg/ml. After about 1 week, cells selected by neomycin were detached and clone cells introduced a human androgen receptor and MMTV-luciferase reporter gene were isolated and obtained by limiting dilution (CHO/MMTV stable transformant).

In the similar manner as above, a stable transformant of SV40 reporter gene was obtained (CHO/SV40 stable transformant).

a) Evaluation of Transcription Activating Action Toward Human Androgen Receptor (Agonistic Action)

CHO/MMTV stable transformant cells and CHO/SV40 stable transformant cells were each seeded to a 96-well luminoplate for cell culture in an amount of $2 \times 10^4$ cells/well. After 6 to 8 hours, each of the compounds of the present invention was added. After about 18 hours from the addition of the compounds, culture medium was removed and 20 μl of a solution containing 1% triton-X and 10% glycerin was added thereto to dissolve the cells and 100 μl of a luciferase substrate solution containing 0.47 mM luciferin was further added thereto. Then, emitted light intensity was measured by means of a luminometer, the intensity being regarded as luciferase activity obtained by MMTV-LTR transcription activation due to human androgen receptor and nonspecific activation of SV40 promoter transcription.

The transcription activating action of the compound of the present invention was calculated according to the following equation as a ratio to the transcription activity induced by 1 nM DHT.

Induction ratio (%)=100(X−B)/(I−B)

I: (MMTV luciferase activity)/(SV40 luciferase activity) in the case that 1 nM DHT is added B: (MMTV luciferase activity)/(SV40 luciferase activity) without treatment X: (MMTV luciferase activity)/(SV40 luciferase activity) in the case that the compound of the present invention is added The agonistic induction ratio of the compound of the present invention [Example 3-12] was found to be 1% or less.

B) Evaluation of Transcription Activation Inhibitory Action Toward Human Androgen Receptor (Antagonistic Action)

CHO/MMTV stable transformant cells and CHO/SV40 stable transformant cells were each inoculated to a 96-well luminoplate for cell culture in an amount of $2\times10^4$ cells. After 6 to 8 hours, each of the compounds of the present invention was added together with DHT (final concentration of 0.3 nM). After about 18 hours from the addition of the compound, 20 μl of a solution containing 1% triton-X and 10% glycerin was added thereto to dissolve the cells and 100 μl of a luciferase substrate solution containing 0.47 mM luciferin was further added thereto. Then, emitted light intensity was measured using a luminometer, the intensity being regarded as luciferase activity-obtained by MMTV-LTR transcription activation due to androgen receptor and nonspecific activation of SV40 promoter transcription.

The transcription activation inhibitory action of the compound of the present invention was calculated according to the following equation as an inhibitory ratio to the transcription activity induced by 0.3 nM DHT.

Inhibitory ratio (%)=100(I'−X')/(I'−B)

I': (MMTV luciferase activity)/(SV40 luciferase activity) in the case that 0.3 nM DHT is only added B: (MMTV luciferase activity)/(SV40 luciferase activity) without treatment X': (MMTV luciferase activity)/(SV40 luciferase activity) in the case that the compound of the present invention is added together with 0.3 nM DHT $IC_{50}$ was determined from the concentration of the compound of the present invention at which the inhibitory ratio calculated by the above method reached 50%.

2. Evaluation of Binding Activity Toward Rat Androgen Receptor.

(1) Preparation of Cytoplasmic Fraction of Rat Prostate

A ventral prostate was taken out from a 20-60 weeks old male Wistar rat after 1 day from testicle-removal. After homogenization and subsequent 800×g×20 minutes of centrifugation, the supernatant was further centrifuged at 223,000×g×60 minutes and the resulting supernatant was recovered to obtain a cytoplasmic fraction.

(2) Measurement of Specific Binding of $^3$H-Mibolerone Toward Prostate Cytoplasmic Androgen Receptor A solution in which the cytoplasmic fraction obtained in (1) was adjusted to 2 mg/ml in terms of a protein concentration was used as a rat androgen receptor solution. To 400 μl of the androgen receptor solution were added $^3$H-mibolerone, triamcinolone acetate, and dimethyl sulfoxide (DMSO) so as to be final concentrations of 1M, 1 μM, and 4%, respectively, whereby a final volume was made 500 μl. After 18 hours of standing at 4° C., 500 μl of a solution containing 0.05% dextran-T70 and 0.5% Durco G-60(Charcoal activated) was added thereto and the whole was mixed. After 15 minutes of standing at 4° C., centrifugation was conducted to recover the supernatant. After 5 ml of Biofluor was added to and mixed with 600 μl of the recovered supernatant, radioactivity was measured to determine a total binding amount of $^3$H-mibolerone to the rat androgen receptor. A nonspecific binding amount was determined by adding a DMSO solution containing non-labeled mibolerone instead of the above DMSO so as to be a non-labeled mibolerone final concentration of 40 μM and conducting the similar operations as above. Difference between the total binding amount and the nonspecific binding amount was regarded as a specific binding amount bound to the androgen receptor.

(3) Inhibitory Activity of the Compound of the Present Invention Against Specific Binding of $^3$H-mibolerone A specific binding amount of $^3$H-mibolerone bound to the rat androgen receptor in the case that the compound of the present invention was present was determined by adding a DMSO solution containing the compound of the present invention in a different concentration together with $^3$H-mibolerone and reacting them in the similar manner as in (2). From the value and the value determined in (2), $IC_{50}$ of the inhibitory activity of the compound of the present invention against specific binding of $^3$H-mibolerone was determined. Furthermore, a dissociation constant Ki was determined from $IC_{50}$ according to the equation of Cheng and Prusoff*.

*: Cheng Y. C. and Prusoff W. H., Relationship between the inhibition constant (Ki) and the concentration of inhibitor which cause 50% inhibition of an enzymatic reaction., Biochem. pharmacol., 22, 3099 (1973)

3. Prostate Gland Reducing Action Toward Mature Male Rat

To a male 9-10 weeks old Wistar rat, the compound of the present invention suspended in a 0.5% methylcellulose solution was orally administered once a day continuously for 15 days. After 6 hours from the final administration, the wet weight of its ventral prostate was measured and a prostate gland reducing of the compound of the present invention was investigated.

The prostate gland reducing of the compound of the present invention was calculated according to the following formula using a group to which the compound of the present invention was administered as a test group and a group to which only methylcellulose was administered as a control group.

Lessening ratio (%)=100(B−A)/B

A: Wet weight of ventral prostate in test group
B: Wet weight of ventral prostate in control group From the lessening ratio determined in the above, an $ED_{50}$ value was calculated by the linear regression method.

On the compounds of the present invention, the following table shows results of prostate gland reducing as an in vitro activity described in 1. b) and as an in vivo activity described in 3.

TABLE 3

| Example | Transcription activation inhibitory action (IC$_{50}$ nM) | Prostate gland reducing (ED$_{50}$ mg/kg) |
|---|---|---|
| 3-9 | 78 | 4.5 |
| 3-12 | 40 | 1.7 |
| 3-15 | 130 | 4.1 |
| 3-23 | 53 | 1.1 |
| 3-30 | 68 | 3.9 |
| Control compound 1 | 80 | 11.3 |
| Control compound 2 | 63 | 9.9 |

Control compound 1: Example 18-4 described in Patent Document 4
Control compound 2: Example 18-7 described in Patent Document 4

As the control compounds, the clinically applicable above two compounds were chosen, which were similar in structure, had clinically a sufficient activity, and also had no observed problematic action such as body weight loss.

This is because the compounds having the strongest binding activity in Patent Document 4, i.e., Examples 13-1 and 21 exhibit a strong prostate-lessening effect but their development as antiandrogenic agents is problematic for the reasons of problems such as a body weight losing action and an agonistic action, and hence they are inadequate as control compounds.

From these test results, it was confirmed that, with regard to the antiandrogenic action of the compound of the present invention, the in vitro activity of the above compound is from ½ to about 2 times but the in vivo activity thereof is unexpectedly strong, i.e., from 2 to 10 times in comparison with the control compounds. This fact shows that the compounds of the present invention are compounds having an excellent oral activity.

Furthermore, since the compounds have an excellent oral activity, they exhibit the effect with a lower dose as compared with conventional compounds, so that they can be formulated as small-size preparations and hence compliance in taking medicine can be also improved.

Moreover, the compounds of the present invention are excellent in solubility in water and hence contrivance for formulation such as solubilization is unnecessary.

Furthermore, these compounds exhibit neither a body weight losing action nor an agonistic action and also the greatest effect is sufficiently strong.

Accordingly, the compounds of the present invention are useful as treating agents of diseases in which androgen acts as a aggravating factor, such as prostate cancer, benign prostatic hyperplasia, virilism, hirsutism, baldness, acne, and seborrhea.

INDUSTRIAL APPLICABILITY

The compounds of the present invention are strong antiandrogenic agents each exhibiting a little influence on sex hormones in the blood without body weight loss and agonist activity. Furthermore, the compounds are excellent in oral activities as compared with conventional compounds.

Therefore, the compounds of the present invention are useful as treating or preventing agents of diseases such as prostate cancer, benign prostatic hyperplasia, virilism, hirsutism, baldness, acne, and seborrhea.

Moreover, the compounds represented by the general formula (IIIa) are useful as intermediates for producing the compounds (I) of the present invention.

What is claimed is:

1. An N-phenyl-(2R,5S)dimethylpiperazine derivative represented by the following general formula (I) or a salt thereof:

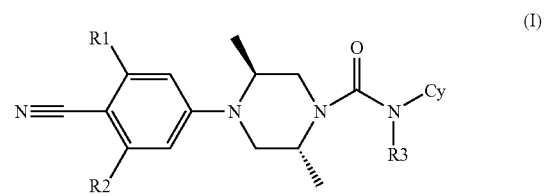

wherein the symbols in the formula have the following meanings:
R$^1$: Cl, F, Br, —CN, —CH$_3$, —CF$_3$, or —O-lower alkyl
R$^2$: H, F, or —OCH$_3$
R$^3$: H or lower alkyl
Cy: pyrimidine substituted by a lower alkyl or a cyclopropyl group.

2. The N-phenyl-(2R,5S)dimethylpiperazine derivative or salt thereof according to claim 1, wherein R$^1$ is Cl, Br, CF$_3$, or —O-lower alkyl and R$^3$ is H or F, and R$^3$ is H.

3. A compound selected from (2R,5S)-4-(3-chloro-4-cyanophenyl)-N-(2-cyclopropylpyrimidin-5-yl)-2,5-dimethylpiperazine-1-carboxamide; and (2R,5S)-4-(4-cyano-3-trifluoromethylphenyl)-N-(2-cyclopropylpyrimidin-5-yl)-2,5-dimethylpiperazine-1-carboxamide, or a salt thereof.

4. A pharmaceutical composition comprising the N-phenyl-(2R,5S)dimethylpiperazine derivative according to claim 1 or a pharmaceutically acceptable salt thereof as an active ingredient.

5. A prostate cancer-treating agent comprising a therapeutically effective amount of the N-phenyl-(2R,5S)dimethylpiperazine derivative according to claim 1 or a pharmaceutically acceptable salt thereof as an active ingredient.

6. A method for treating prostate cancer which comprises administering a therapeutically effective amount of the N-phenyl-(2R,5S)dimethylpiperazine derivative according to claim 1 or a pharmaceutically acceptable salt thereof.

7. A compound selected from
(2R,5S)-4-[4-cyano-3-(trifluoromethyl)phenyl]-2,5-dimethyl-N-(2-methylpyrimidin-5-yl)pip erazine-1-caxboxamide;
(2R,5S)-4-[4-cyano-3-(trifluoromethyl)phenyl]-N-(2-clopropy)pyrimidin-5-yl)-2,5-di methylpiperazine-1-carboxamide;
(2R,5S)-4-(3-chloro-4-cyanophenyl)-2,5-dimethyl-N-(2-methylpyrimidin-5-yl)piperazin e-1-carboxamide; (2R,5S)-4-(3-chloro-4-cyanobenyl)-N-(2-cyclopropylpyrimidin-5-yl)-2,5-dimethylpiper azine-1-carboxamide;
(2R,5S)-4-(4-cyano-3-methoxyphenyl)-N-(2-cyclopropylpyrimidin-5-yl)-2,5-dimethylpi perazine-1-carboxanxide;
(2R,5S)-4-(4-cyan-3-fluoro-5-methoxyphenyl)-N-(2-cyclopropylpyrimidin-5-yl)-2,5-di methylpiperazine-1-carboxamide;
(2R,5S)-4-(3-bromo-4-cyanophenyl)-N-(2-cyclopropylpyrimidin-5-yl)-2,5-dimethylpiper azine-1-carboxamide; and
(2R,5S)-4-(3-bromo-4-cyanophenyl)-2,5-dimethyl-N-(2-methylpyrimidin-5-yl)piperazin e-1-carboxamide, or a salt thereof.

* * * * *

UNITED STATES PATENT AND TRADEMARK OFFICE
CERTIFICATE OF CORRECTION

PATENT NO. : 7,297,698 B2  Page 1 of 1
APPLICATION NO. : 10/521119
DATED : November 20, 2007
INVENTOR(S) : Nobuaki Taniguchi et al.

It is certified that error appears in the above-identified patent and that said Letters Patent is hereby corrected as shown below:

Claim 2 (Column 46, line 23): Please delete "$CF_3$", and insert -- -$CF_3$ --
Claim 2 (Column 46, line 24): Please delete "$R^3$", and insert --$R^2$--
Claim 7 (Column 46, line 44): Please delete "(2-methylpyrimidin-5-yl)pip erazine", and insert --(2-methylpyrimidin-5-yl)piperazine--
Claim 7 (Column 46, lines 46-47): Please delete "(2-cy-clopropy)pyrimidin-5-yl)", and insert --(2-cyclopropylpyrimidin-5-yl)--
Claim 7 (Column 46, line 47): Please delete "2,5-di methylpiperazine", and insert --2,5-dimethylpiperazine--
Claim 7 (Column 46, line 50): Please start new paragraph with (2R
Claim 7, (Column 46, line 51): Please delete "(3-chloro-4-cyanopbenyl)" and insert --(3-chloro-4-cyanophenyl)--
Claim 7 (Column 46, line 52): Please delete "2,5-dimethylpiper azine" and insert --2,5-dimethylpiperazine--
Claim 7 (Column 46, line 54): Please delete "2,5-dimethylpi perazine", and insert --2,5-dimethylpiperazine--
Claim 7 (Column 46, line 56): Please delete "cyan", and insert --cyano--
Claim 7 (Column 46, line 57): Please delete "2,5-di methylpiperazine", and insert --2,5-dimethylpiperazine--
Claim 7 (Column 46, line 60): Please delete "2,5-dimethylpiper azine" and insert --2,5-dimethylpiperazine--
Claim 7 (Column 46, line 63): Please delete "piperazin e" and insert --piperazine--

Signed and Sealed this

Thirteenth Day of May, 2008

JON W. DUDAS
*Director of the United States Patent and Trademark Office*